United States Patent
Frayne et al.

(10) Patent No.: US 9,951,350 B2
(45) Date of Patent: Apr. 24, 2018

(54) METHODS OF PREPARING CELLS AND COMPOSITIONS

(71) Applicants: Jan Frayne, Bristol (GB); David Anstee, Bristol (GB)

(72) Inventors: Jan Frayne, Bristol (GB); David Anstee, Bristol (GB)

(73) Assignee: NHS Blood & Transplant, Watford (GB)

( * ) Notice: Subject to any disclaimer, the term of this patent is extended or adjusted under 35 U.S.C. 154(b) by 0 days.

(21) Appl. No.: 14/371,603

(22) PCT Filed: Jan. 11, 2013

(86) PCT No.: PCT/GB2013/050043
§ 371 (c)(1),
(2) Date: Jul. 10, 2014

(87) PCT Pub. No.: WO2013/104909
PCT Pub. Date: Jul. 18, 2013

(65) Prior Publication Data
US 2014/0377237 A1  Dec. 25, 2014

(30) Foreign Application Priority Data
Jan. 11, 2012 (GB) .................................. 1200458.6

(51) Int. Cl.
| | |
|---|---|
| C12N 15/87 | (2006.01) |
| C12N 5/10 | (2006.01) |
| C12N 15/00 | (2006.01) |
| A61K 35/18 | (2015.01) |
| A61K 38/42 | (2006.01) |
| C12N 15/85 | (2006.01) |
| C12N 5/078 | (2010.01) |

(52) U.S. Cl.
CPC .............. *C12N 15/85* (2013.01); *A61K 35/18* (2013.01); *C12N 5/0641* (2013.01); *A61K 38/42* (2013.01); *C12N 2800/107* (2013.01)

(58) Field of Classification Search
None
See application file for complete search history.

(56) References Cited

FOREIGN PATENT DOCUMENTS

WO  WO-2007/095064 A2  8/2007

OTHER PUBLICATIONS

Guo et al, Protein tolerance to random amino acid change, PNAS, 2004, vol. 101 (25), pp. 9205-9210.*
Lesk et al, Prediction of Protein Function from Protein Sequence and Structure, p. 27 and 28, downloaded Sep. 16, 2007.*
Mazurier et al, Red blood cells from induced pluripotent stem cells: hurdles and developments, Current Opinion in Hematology 2011, 18:249-253.*
Trakarnsanga et al, Induction of adult levels of-globin in human erythroid cells that intrinsically express embryonic or fetal globin by transduction with KLF1 and BCL11A-XL, haematologica, 2014, pp. 1677-1685.*
Hattangadi et al, From stem cell to red cell: regulation of erythropoiesis at multiple levels by multiple proteins, RNAs, and chromatin modifications, Blood, 2011, pp. 6258-6268.*
Hiroyama et al, Establishment of Mouse Embryonic Stem Cell-Derived Erythroid Progenitor Cell Lines Able to Produce Functional Red Blood Cells, PLoS One, 2008, pp. 1-11.*
Sankaran et al, Human Fetal Hemoglobin Expression is Regulated by the Developmental Stage-Specific Repressor BCL11A, Science, 2008, pp. 1839-1842.*
Armstrong et al., A SWI/SNF-related chromatin remodeling complex, E-RC1, is required for tissue-specific transcriptional regulation by EKLF in vitro, Cell, 95(1):93-104 (1998).
Bender et al., Beta-globin gene switching and DNase I sensitivity of the endogenous beta-globin locus in mice do not require the locus control region, Mol. Cell, 5(2):387-93 (2000).
Bieker, Probing the onset and regulation of erythroid cell-specific gene expression, Mt. Sinai J. Med., 72(5):333-8 (2005).
Dillon et al., Human gamma-globin genes silenced independently of other genes in the beta-globin locus, Nature, 350(6315):252-4 (1991).
Drissen et al., The active spatial organization of the beta-globin locus requires the transcription factor EKLF, Genes Dev., 18(20):2485-90 (2004).
Drissen et al., The erythroid phenotype of EKLF-null mice: defects in hemoglobin metabolism and membrane stability, Mol. Cell Biol., 25(12):5205-14 (2005).
Forrester et al., A developmentally stable chromatin structure in the human beta-globin gene cluster, Proc. Natl. Acad. Sci. USA, 83(5):1359-63 (1986).
Funnell et al., Erythroid Krüppel-like factor directly activates the basic Krüppel-like factor gene in erythroid cells, Mol. Cell Biol., 27(7):2777-90 (2007).
Griffiths et al., Maturing reticulocytes internalize plasma membrane in glycophorin A-containing vesicles that fuse with autophagosomes before exocytosis, Blood, 119(26):6296-306 (2012).
Grosveld et al., Position-independent, high-level expression of the human beta-globin gene in transgenic mice, Cell, 51(6):975-85 (1987).
Hodge et al., A global role for EKLF in definitive and primitive erythropoiesis, Blood, 107(8):3359-70 (2006).
Im et al., Chromatin domain activation via GATA-1 utilization of a small subset of dispersed GATA motifs within a broad chromosomal region, Proc. Natl. Acad. Sci. USA, 102(47):17065-70 (2005).
International Preliminary Report on Patentability, International Application No. PCT/GB2013/050043, dated Jul. 15, 2014.
International Search Report and Written Opinion, International Application No. PCT/GB2013/050043, dated Jun. 18, 2013.
Kaufman et al., Toward clinical therapies using hematopoietic cells derived from human pluripotent stem cells, Blood, 114(17):3513-23 (2009).

(Continued)

*Primary Examiner* — Maria Marvich
(74) *Attorney, Agent, or Firm* — Marshall, Gerstein & Borun LLP

(57) ABSTRACT

The present invention provides a method of preparing adult red blood cells from stem cells in vitro using certain transcription factors for use in medicine, transfusions and transplants. The invention also provides blood compositions with cells prepared by the method.

18 Claims, 14 Drawing Sheets

(56) References Cited

OTHER PUBLICATIONS

Figure 2A:
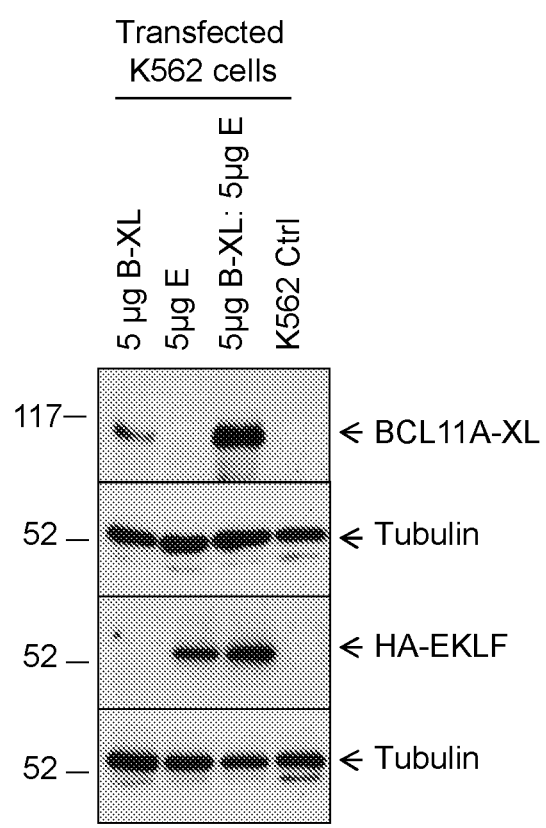

Lettre et al., DNA polymorphisms at the BCL11A, HBS1L-MYB, and beta-globin loci associate with fetal hemoglobin levels and pain crises in sickle cell disease, Proc. Natl. Acad. Sci. USA, 105(33):11869-74 (2008).
Liu et al., Functional studies of BCL11A: characterization of the conserved BCL11A-XL splice variant and its interaction with BCL6 in nuclear paraspeckles of germinal center B cells, Mol. Cancer, 5:18 (2006).
Menzel et al., A QTL influencing F cell production maps to a gene encoding a zinc-finger protein on chromosome 2p15, Nat. Genet., 39(10):1197-9 (2007).
Miller et al., A novel, erythroid cell-specific murine transcription factor that binds to the CACCC element and is related to the Krüppel family of nuclear proteins, Mol. Cell Biol., 13(5):2776-86 (1993).
Noordermeer et al., Joining the loops: beta-globin gene regulation, IUBMB Life, 60(12):824-33 (2008).
Ouyang et al., Regulation of erythroid Krüppel-like factor (EKLF) transcriptional activity by phosphorylation of a protein kinase casein kinase II site within its interaction domain, J. Biol. Chem., 273(36):23019-25 (1998).
Peyrard et al., Banking of pluripotent adult stem cells as an unlimited source for red blood cell production: potential applications for alloimmunized patients and rare blood challenges, Transfus. Med. Rev., 25(3):206-16 (2011).
Pilon et al., Failure of terminal erythroid differentiation in EKLF-deficient mice is associated with cell cycle perturbation and reduced expression of E2F2, Mol. Cell Biol., 28(24):7394-401 (2008).
Raich et al., Autonomous developmental control of human embryonic globin gene switching in transgenic mice, Science, 250(4984):1147-9 (1990).
Sabatino et al., Substitution of the human beta-spectrin promoter for the human agamma-globin promoter prevents silencing of a linked human beta-globin gene in transgenic mice, Mol. Cell Biol., 18(11):6634-40 (1998).
Sankaran et al., Human fetal hemoglobin expression is regulated by the developmental stage-specific repressor BCL11A, Science, 322(5909):1839-42 (2008).
Sankaran et al., Developmental and species-divergent globin switching are driven by BCL11A, Nature, 460:1093-7 (2009).
Sedgewick et al., BCL11A is a major HbF quantitative trait locus in three different populations with beta-hemoglobinopathies, Blood Cells Mol. Dis., 41(3):255-8 (2008).
Shyu et al., Regulation of globin gene switch by nuclear transport processes of transcription factors, Blood Cells, Molecules and Diseases, 38(2):131 (2007).
Siatecka et al., The multifunctional role of EKLF/KLF1 during erythropoiesis, Blood, 118(8):2044-54 (2011).
Singleton et al., Mutations in EKLF/KLF1 form the molecular basis of the rare blood group In(Lu) phenotype, Blood, 112(5):2081-8 (2008).
Tallack et al., KLF1 directly coordinates almost all aspects of terminal erythroid differentiation, IUBMB Life, 62(12):886-90 (2010).
Tanavde et al., Human stem-progenitor cells from neonatal cord blood have greater hematopoietic expansion capacity than those from mobilized adult blood, Exp. Hematol., 30(7):816-23 (2002).
Tuan et al., The "beta-like-globin" gene domain in human erythroid cells, Proc. Natl. Acad. Sci. USA, 82(19):6384-8 (1985).
Uda et al., Genome-wide association study shows BCL11A associated with persistent fetal hemoglobin and amelioration of the phenotype of beta-thalassemia, Proc. Natl. Acad. Sci. USA, 105(5):1620-5 (2008).
Wijgerde et al., The role of EKLF in human beta-globin gene competition, Genes Dev., 10(22):2894-902 (1996).
Wijgerde et al., Transcription complex stability and chromatin dynamics in vivo, Nature, 377(6546):209-13 (1995).
Xu et al., Correction of Sickle Cell Disease in Adult Mice by Interference with Fetal Hemoglobin Silencing, Science, 334:993-6 (2011).
Xu et al., Transcriptional silencing of {gamma}-globin by BCL11A involves long-range interactions and cooperation with SOX6, Genes Dev., 24(8):783-98 (2010).
Zhang et al., Acetylation and modulation of erythroid Krüppel-like factor (EKLF) activity by interaction with histone acetyltransferases, Proc. Natl. Acad. Sci. USA, 95(17):9855-60 (1998).
Zhang et al., Site-specific acetylation by p300 or CREB binding protein regulates erythroid Krüppel-like factor transcriptional activity via its interaction with the SWI-SNF complex, Mol. Cell Biol., 21(7):2413-22 (2001).
Zhou et al., KLF1 regulates BCL11A expression and gamma- to beta-globin gene switching, Nat. Genet., 42(9):742-4 (2010).

\* cited by examiner

Figure 1A-C
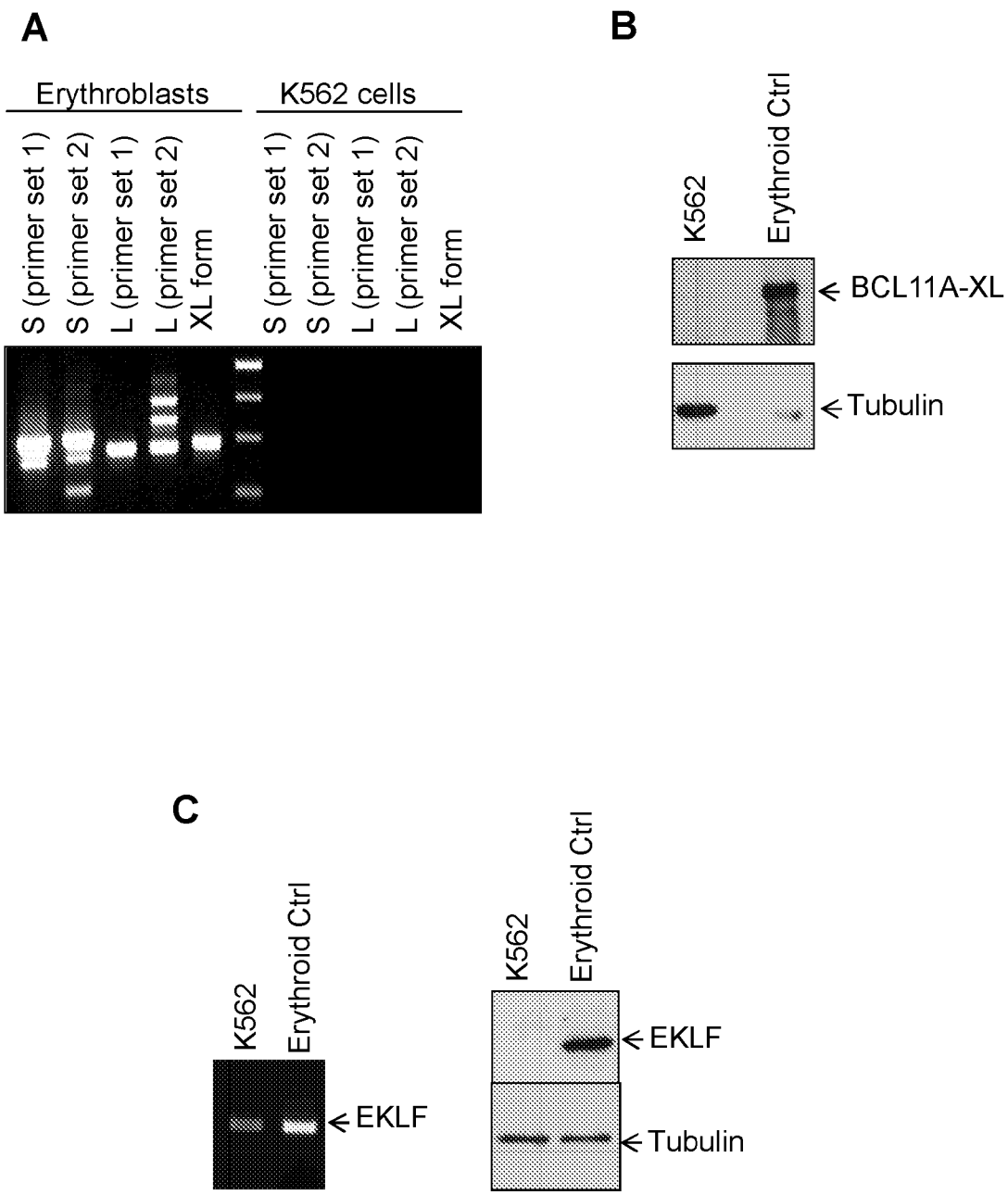

Figure 2B-C
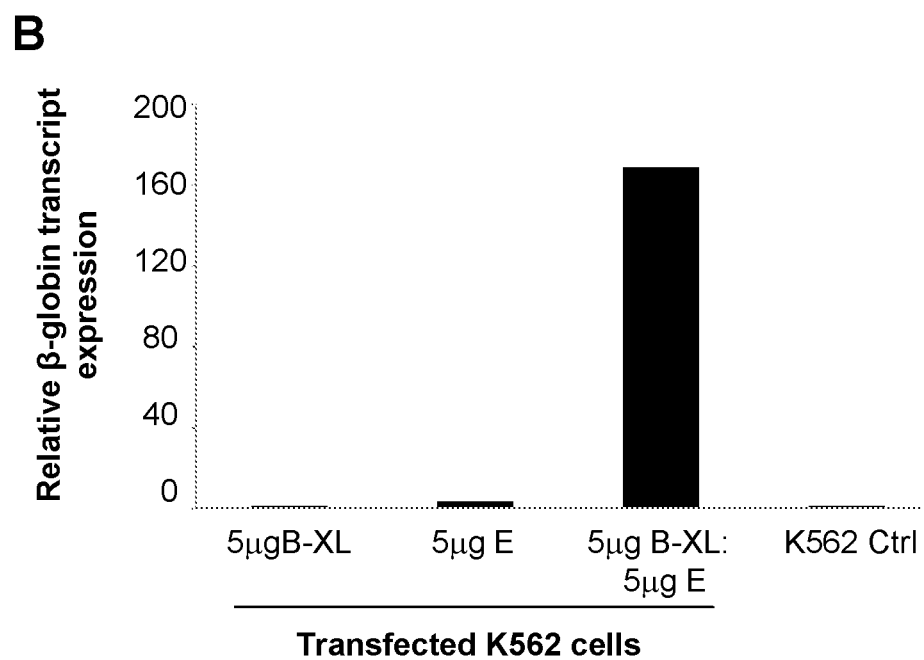
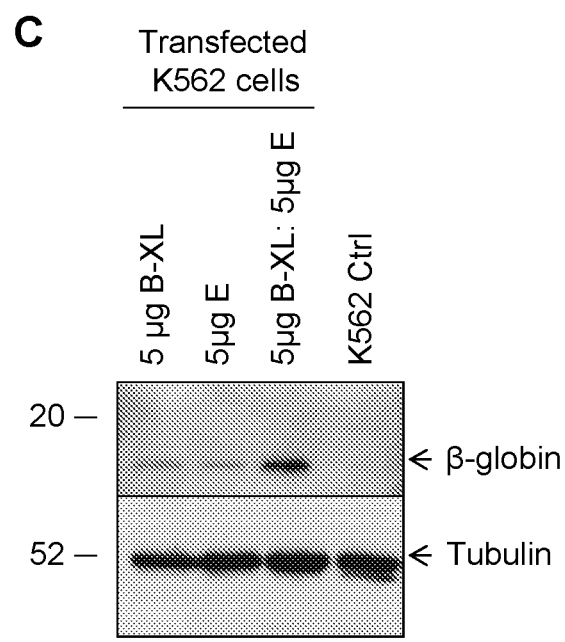

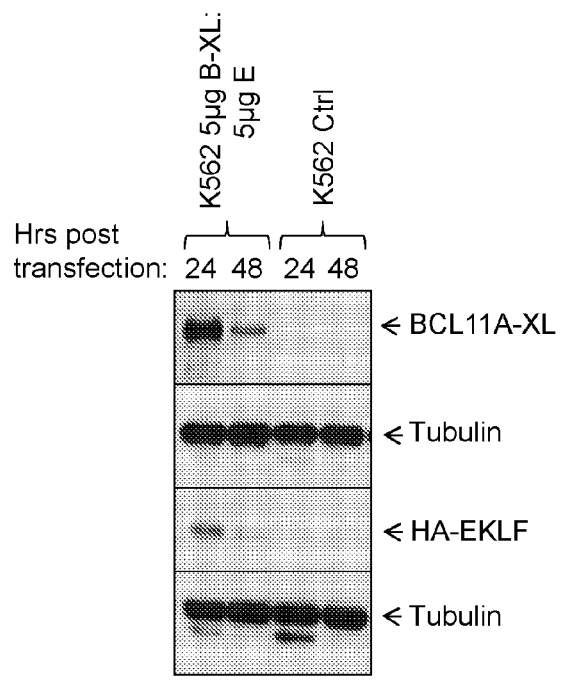

Figure 3C-D
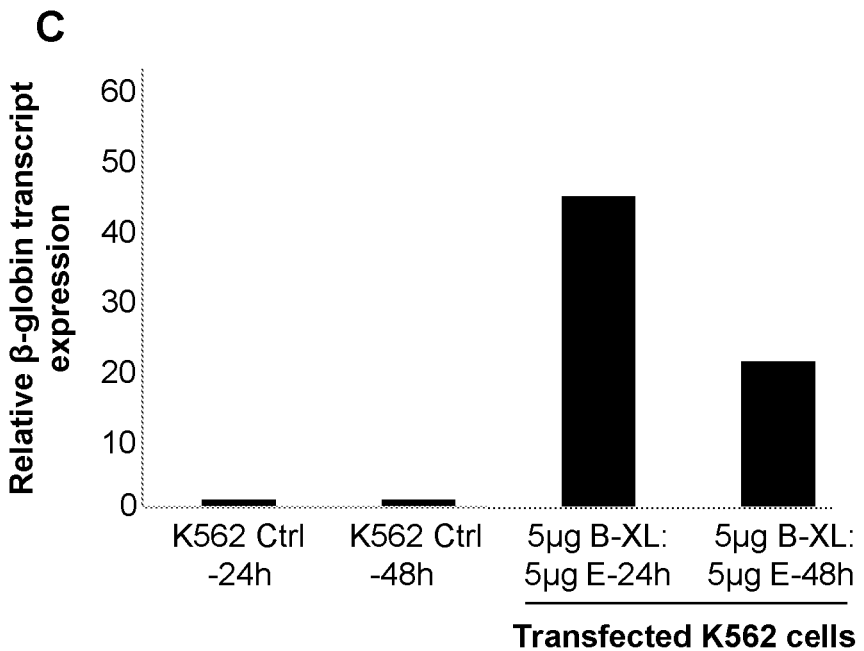
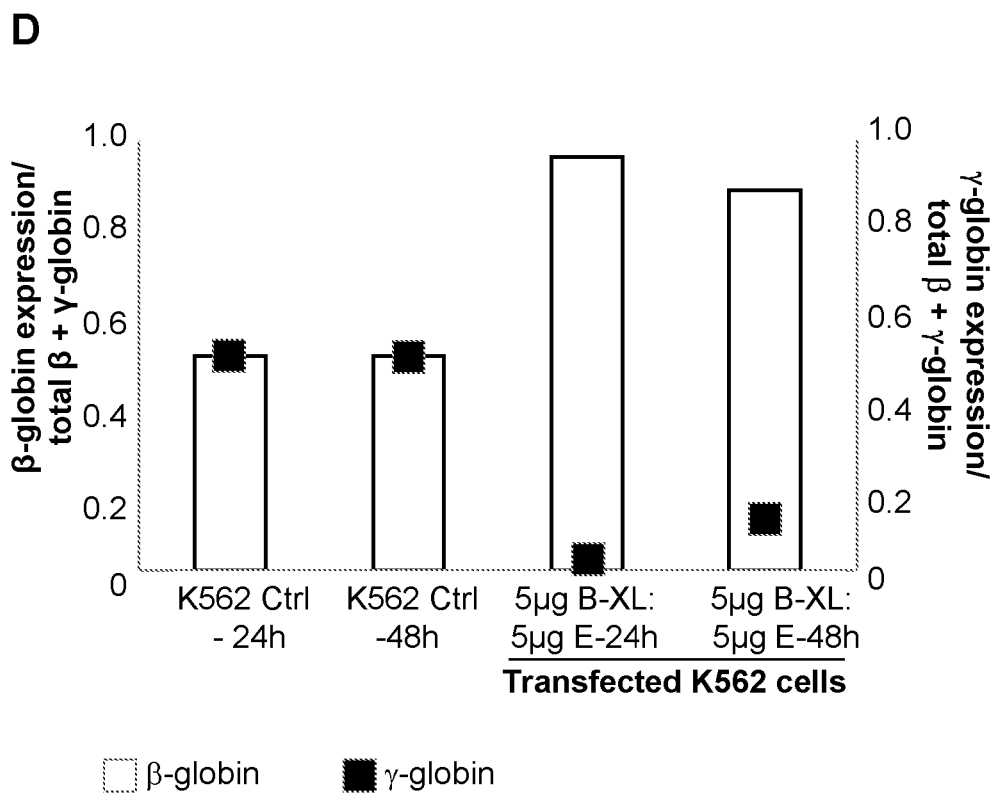

Figure 4B-C
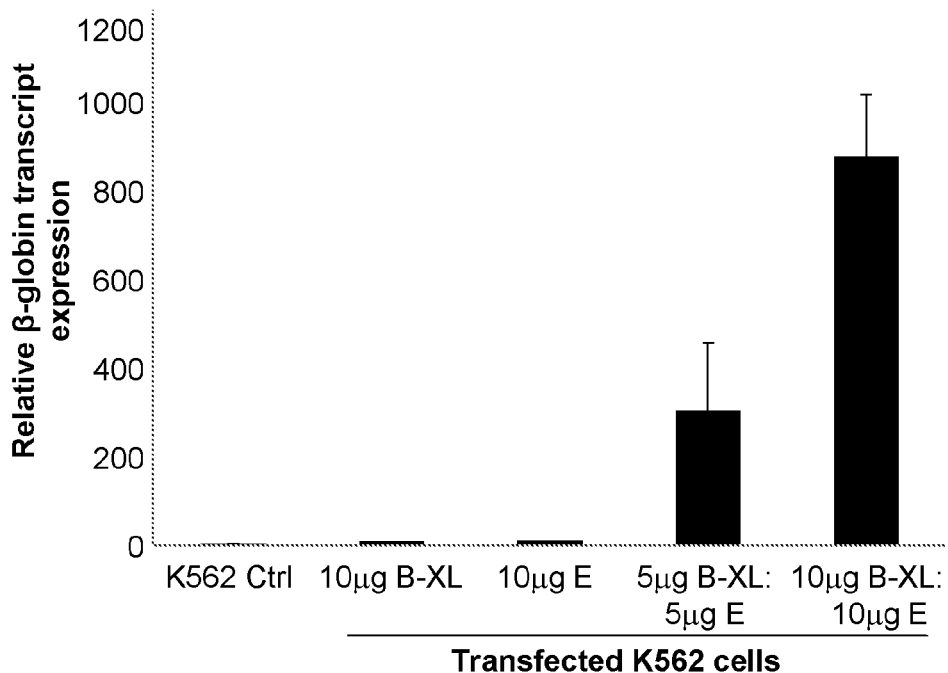
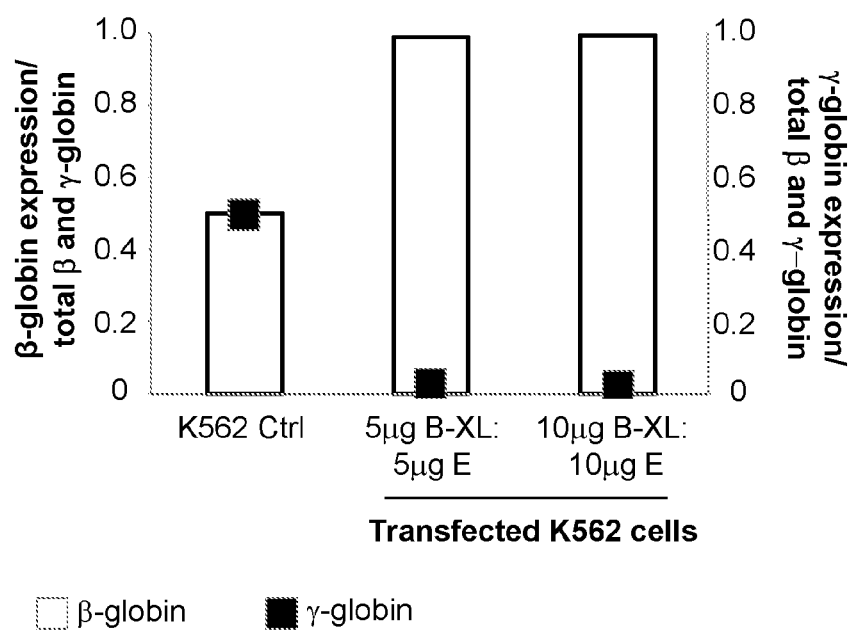

Figure 4D-E
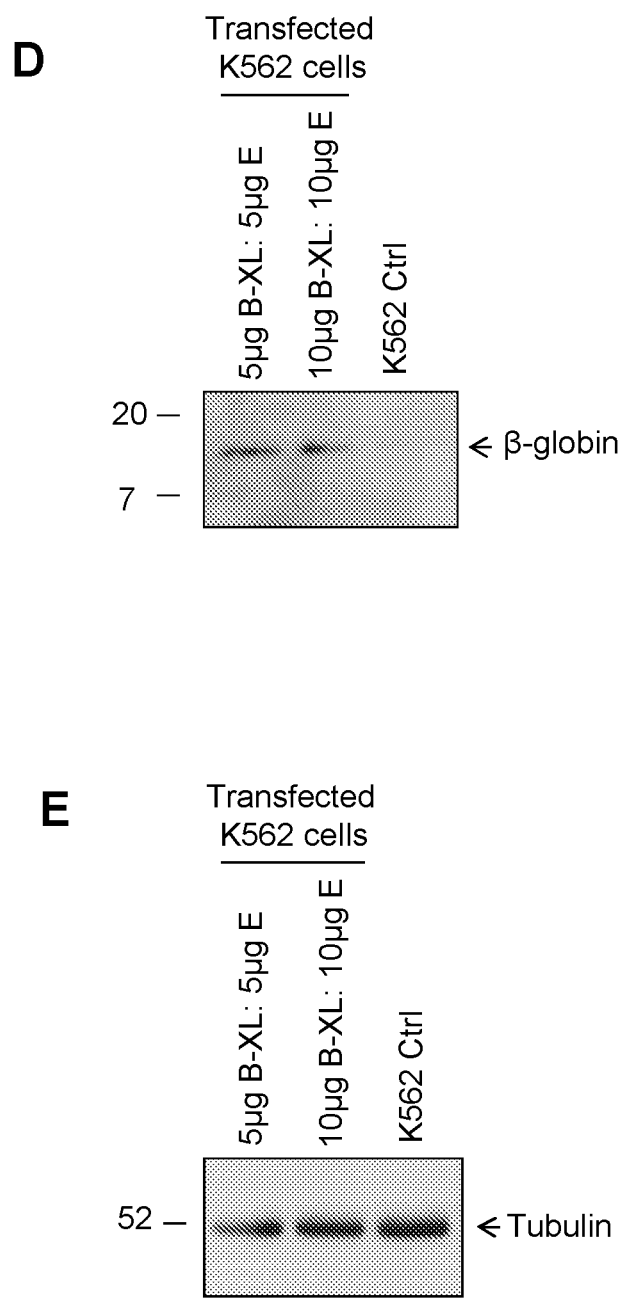

Figure 5A-B
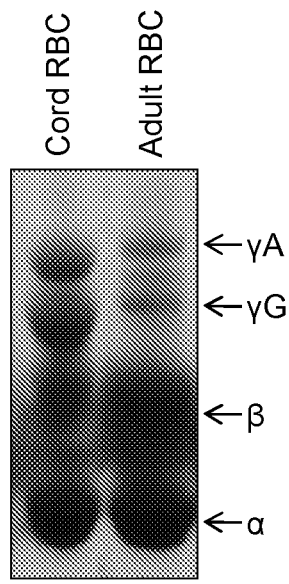
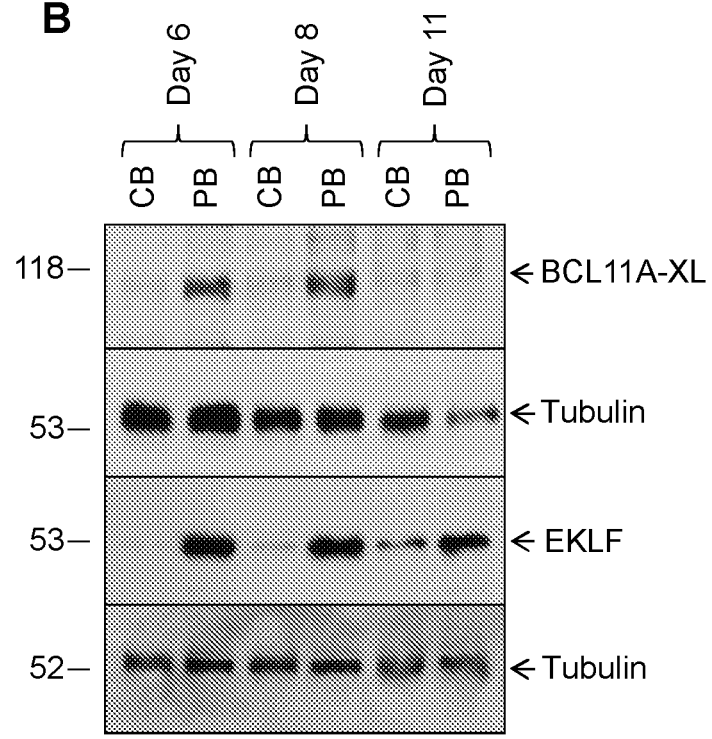

Figure 6B-C
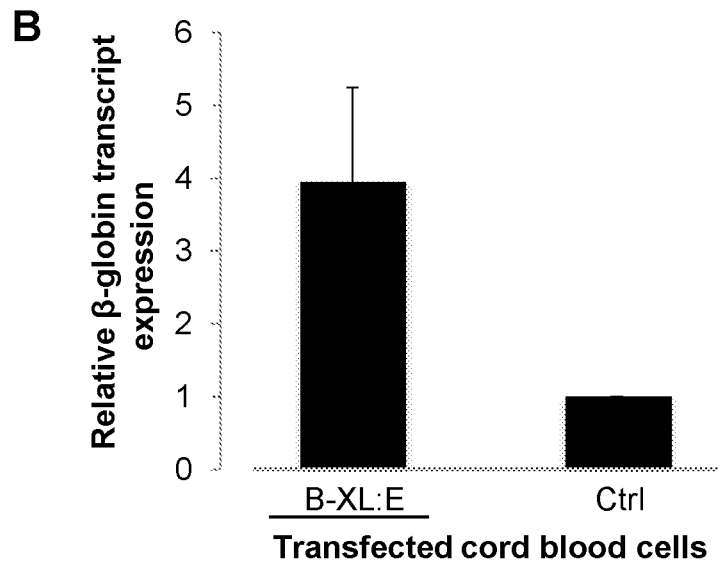
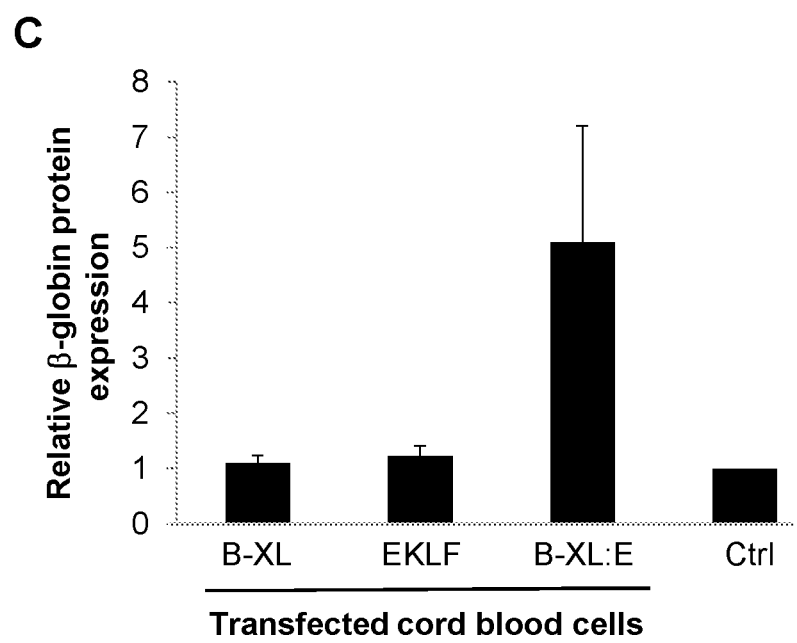

Figure 7A-C
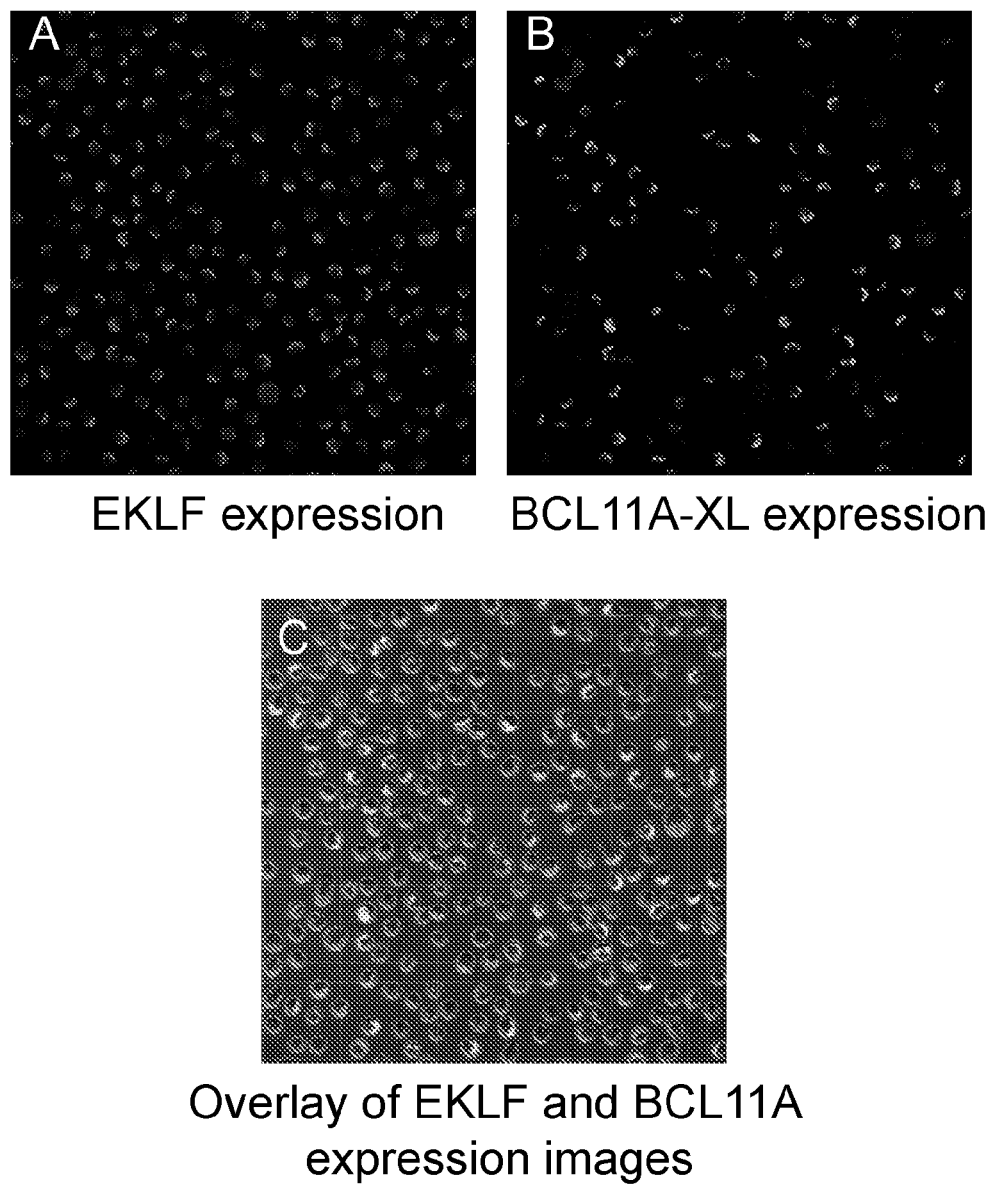
EKLF expression    BCL11A-XL expression
Overlay of EKLF and BCL11A expression images

SEQUENCE LISTING

```
<160> NUMBER OF SEQ ID NOS: 22

<210> SEQ ID NO 1
<211> LENGTH: 36
<212> TYPE: DNA
<213> ORGANISM: Artificial Sequence
<220> FEATURE:
<223> OTHER INFORMATION: Synthetic Primer

<400> SEQUENCE: 1
```

```
gattacgctg aattctcatg gcccacagcc gagacc                              36

<210> SEQ ID NO 2
<211> LENGTH: 34
<212> TYPE: DNA
<213> ORGANISM: Artificial Sequence
<220> FEATURE:
<223> OTHER INFORMATION: Synthetic Primer

<400> SEQUENCE: 2
gatactcgag aattctcaaa ggtggcgctt catg                                34

<210> SEQ ID NO 3
<211> LENGTH: 20
<212> TYPE: DNA
<213> ORGANISM: Artificial Sequence
<220> FEATURE:
<223> OTHER INFORMATION: Synthetic Primer

<400> SEQUENCE: 3
agatcccttc cttagcttcg                                                20

<210> SEQ ID NO 4
<211> LENGTH: 20
<212> TYPE: DNA
<213> ORGANISM: Artificial Sequence
<220> FEATURE:
<223> OTHER INFORMATION: Synthetic Primer

<400> SEQUENCE: 4
tcaacactcg atcactgtgc                                                20

<210> SEQ ID NO 5
<211> LENGTH: 20
<212> TYPE: DNA
<213> ORGANISM: Artificial Sequence
<220> FEATURE:
<223> OTHER INFORMATION: Synthetic Primer

<400> SEQUENCE: 5
gacgatggca ctgttaatgg                                                20

<210> SEQ ID NO 6
<211> LENGTH: 20
<212> TYPE: DNA
<213> ORGANISM: Artificial Sequence
<220> FEATURE:
<223> OTHER INFORMATION: Synthetic Primer

<400> SEQUENCE: 6
gggtgtgtga agaacaagtg                                                20

<210> SEQ ID NO 7
<211> LENGTH: 20
<212> TYPE: DNA
<213> ORGANISM: Artificial Sequence
<220> FEATURE:
<223> OTHER INFORMATION: Synthetic Primer

<400> SEQUENCE: 7
aatgggggtg tgtgaagaac                                                20

<210> SEQ ID NO 8
<211> LENGTH: 20
<212> TYPE: DNA
<213> ORGANISM: Artificial Sequence
```

```
<220> FEATURE:
<223> OTHER INFORMATION: Synthetic Primer

<400> SEQUENCE: 8
catgacctcc tcacctgtgg                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic Primer

<400> SEQUENCE: 9
ggtgtgtgaa gaacccgcgg                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic Primer

<400> SEQUENCE: 10 atggggtgt gtgaagaacc                                               20

<210> SEQ ID NO 11
<211> LENGTH: 18
<212> TYPE: DNA
<213> ORGANISM: Artificial Sequence
<220> FEATURE:
<223> OTHER INFORMATION: Synthetic Primer

<400> SEQUENCE: 11
gccctccatc agcacact                                                18

<210> SEQ ID NO 12
<211> LENGTH: 19
<212> TYPE: DNA
<213> ORGANISM: Artificial Sequence
<220> FEATURE:
<223> OTHER INFORMATION: Synthetic Primer

<400> SEQUENCE: 12
gatcctccga acccaaaag                                               19

<210> SEQ ID NO 13
<211> LENGTH: 21
<212> TYPE: DNA
<213> ORGANISM: Artificial Sequence
<220> FEATURE:
<223> OTHER INFORMATION: Synthetic Primer

<400> SEQUENCE: 13
atatgatgtg cccgactatg c                                            21

<210> SEQ ID NO 14
<211> LENGTH: 19
<212> TYPE: DNA
<213> ORGANISM: Artificial Sequence
<220> FEATURE:
<223> OTHER INFORMATION: Synthetic Primer

<400> SEQUENCE: 14
gatcctccga acccaaaag                                               19
```

```
<210> SEQ ID NO 15
<211> LENGTH: 20
<212> TYPE: DNA
<213> ORGANISM: Artificial Sequence
<220> FEATURE:
<223> OTHER INFORMATION: Synthetic Primer

<400> SEQUENCE: 15
ctttagtgat ggcctggctc                                                    20

<210> SEQ ID NO 16
<211> LENGTH: 20
<212> TYPE: DNA
<213> ORGANISM: Artificial Sequence
<220> FEATURE:
<223> OTHER INFORMATION: Synthetic Primer

<400> SEQUENCE: 16
ggcagaatcc agatgctcaa                                                    20

<210> SEQ ID NO 17
<211> LENGTH: 21
<212> TYPE: DNA
<213> ORGANISM: Artificial Sequence
<220> FEATURE:
<223> OTHER INFORMATION: Synthetic Primer

<400> SEQUENCE: 17
gcaaggtgaa cgtggatgaa g                                                  21

<210> SEQ ID NO 18
<211> LENGTH: 23
<212> TYPE: DNA
<213> ORGANISM: Artificial Sequence
<220> FEATURE:
<223> OTHER INFORMATION: Synthetic Primer

<400> SEQUENCE: 18
tcaccttagg gttgcccata act                                                23

<210> SEQ ID NO 19
<211> LENGTH: 22
<212> TYPE: DNA
<213> ORGANISM: Artificial Sequence
<220> FEATURE:
<223> OTHER INFORMATION: Synthetic Primer

<400> SEQUENCE: 19
gggcaaggtg aatgtggaag at                                                 22

<210> SEQ ID NO 20
<211> LENGTH: 21
<212> TYPE: DNA
<213> ORGANISM: Artificial Sequence
<220> FEATURE:
<223> OTHER INFORMATION: Synthetic Primer

<400> SEQUENCE: 20
gggtccatgg gtagacaacc a                                                  21

<210> SEQ ID NO 21
<211> LENGTH: 22
<212> TYPE: DNA
<213> ORGANISM: Artificial Sequence
<220> FEATURE:
<223> OTHER INFORMATION: Synthetic Primer
```

```
<400> SEQUENCE: 21
agctgttccc aaccctgtaa tc                                              22

<210> SEQ ID NO 22
<211> LENGTH: 23
<212> TYPE: DNA
<213> ORGANISM: Artificial Sequence
<220> FEATURE:
<223> OTHER INFORMATION: Synthetic Primer

<400> SEQUENCE: 22
ggatagtatg cagcacggtt ctg                                             23
```

METHODS OF PREPARING CELLS AND COMPOSITIONS

The present invention relates to a method of preparing adult red blood cells in vitro for diagnostic and therapeutic use in medicine, transfusions and transplants. The invention also provides blood compositions with such cells prepared by the method.

Red blood cells (RBCs) or erythrocytes, from whole blood are used extensively in medicine, blood transfusions and surgery as a lifesaving treatment for anaemia and as reagents for detecting and determining the specificity of alloantibodies present in patient sera in order to allow the selection of compatible blood for transfusion. Presently, the main source of adult red blood cells is to isolate them from whole blood donated by an adult blood donor. Currently, there is a need for an alternative supply of cultured cells of adult phenotype particularly with uncommon blood group phenotypes and more generally to cover shortages in the availability of blood for transfusion when patient requirements exceed blood available from donations.

All red blood cells have haemoglobin as a major component. Hemoglobin is an oxygen carrier protein essential for respiration. Most types of normal haemoglobin, including haemoglobin A, haemoglobin A2, and haemoglobin F, are tetramers composed of four protein subunits and four heme prosthetic groups. Whereas adult haemoglobin (HbA) is composed of two alpha and two beta subunits, fetal haemoglobin (HbF) is composed of two alpha and two gamma subunits, commonly denoted as α2γ2. Because of its presence in fetal haemoglobin, the gamma subunit is commonly called the "fetal" haemoglobin subunit.

The transition from fetal to adult haemoglobin occurs during the first 4-6 months after birth. HbF has a greater affinity for oxygen than HbA and this property is advantageous to the foetus in utero because it facilitates transfer of oxygen from the mother to the foetus. However this property is not optimal in the adult because oxygen from HbF is less readily released to the tissues.

The human β-globin locus on chromosome 11 contains the embryonic (ε), fetal (Gγ and Aγ), and adult (β) globin genes that are expressed sequentially during development. Upstream of the locus, a cis-regulatory element known as the locus control region (LCR) is essential for high level expression of the globin genes [1-4]. Interaction of the LCR with the globin genes is achieved by long range interactions and chromosomal looping which brings the promoter of the actively expressed globin gene in close spatial proximity to the LCR [5]. The LCR up-regulates only one gene at a time with the globin genes competing with each other for interaction with the LCR [6] with one determinant for interaction being relative distance of the gene from the LCR. In adult cells, the final switch from fetal to the more distant β globin gene is achieved by active silencing of the fetal genes [7-9]. This switch from fetal to adult globin has been a subject of intense study due to its clinical significance, and to date much work has focused on treatments that reactivate γ-globin expression in adult cells to ameliorate the severity of β-hemoglobinopathies such as sickle cell disease and the β-thalassemias. However, the molecular mechanisms regulating the switch are far from elucidated.

The generation of RBCs in vitro for transfusion purposes is a major goal of health services globally as such technologies have the potential to provide replenishable supplies of transfusion product with reduced risk of infectious agents and resolve complex alloimmunisation issues and the availability of rare blood group products. In recent years, advances in the development of systems for the generation of erythrocytes in vitro have progressed rapidly using progenitor cells isolated from peripheral blood, umbilical cord blood and human pluripotent stem cells (embryonic stem cells (ESCs) and induced pluripotent stem cells (iPSCs)).

Cells from all progenitor sources can be induced to differentiate efficiently down the erythroid pathway. However, progenitors isolated from umbilical cord blood have the distinct advantage of a greater expansion capacity than those isolated from peripheral blood [10]. ESCs and iPSCs have the potential to provide an inexhaustible source of progenitors for the generation of high volumes of RBCs and to facilitate the innovative development of allogeneic and rare blood group products for transfusion purposes [11, 12]. However, although cord blood, ESCs and iPSCs offer an attractive and realistic therapeutic potential one hurdle still unresolved is failure of the differentiating erythroblasts to undergo the switch from γ- to β-globin expression, resulting in erythrocytes expressing predominantly or exclusively fetal globins.

The limited proliferative capacity of erythroid progenitors derived from peripheral blood limits the number of red cells that can be obtained by in vitro culture methods and greatly impacts the economic viability of producing therapeutic quantities of red cells from this source. Conventional red cell products obtained from donors contain a mixture of red cells at different ages. In contrast, cultured red cells are all nascent and likely to survive for the same prolonged period of time in the peripheral circulation. Patients requiring regular blood transfusions (e.g. patients with sickle cell disease, thalassemia, myelodysplastic syndrome) suffer from organ damage as a result of iron overload from repeated transfusions. Because of the increased life span in vivo of cultured red cells it can be anticipated that patients of this type would need less frequent transfusions and consequently the problems of iron overload would be ameliorated. The risks associated with donor blood such as viral contamination and existence of prions could be avoided by using in vitro generated red blood cells.

WO2007/095064 discloses erythroid cells that have been derived from human embryonic stem cells which intrinsically express both adult and fetal haemoglobin as determined by PCR when cultured in a media for 30 days.

The present invention seeks to address some of the challenges in this field. According to the present invention there is provided a method of preparing adult red blood cells comprising the steps of obtaining stem cells, or cell lines from a source, culturing the cells in a defined medium and modifying said cells in vitro with one or more transcription factors to convert fetal globin into adult globin.

The method may increase or induce the expression of adult β-globin and/or suppress the expression of fetal γ-globin.

The cells that are obtained may express fetal haemoglobin.

The method may further include conversion of the cells from a fetal phenotype to an adult phenotype.

The method may have an additional step of enucleation of cells where the cells are derived from induced pluripotent stem cells (iPSC) or ESC cells.

The cells selected or isolated from the source may express surface antigen CD34. The cells may be modified to express one or more transcription factors.

The transcription factor may be selected from BCL11A, other isoforms of BCL11A, EKLF, tagged forms of EKLF, GATA 1, FOG 1, SCL, SOX6 and any variants thereof. The cells may be obtained from umbilical cord blood, induced pluripotent stem cells, erythropoietic stem cells, or erythropoietic cells lines.

In one embodiment a combination of BCL11A and EKLF is used to convert fetal globin into adult globin in umbilical cord blood derived cells.

The cell culture and modifications may be conducted in vitro.

The culture media comprises at least one of serum, fetal bovine serum, insulin, heparin, transferrin. The media may be further supplemented with at least one of SCF, EPO (erythropoietin) or iron saturated transferrin.

In a further aspect of this invention there is provided red blood cells prepared according to the present method.

According to another aspect of the present invention there is provided red blood cells with adult phenotype composed of cultured stem cells modified in vitro to have an adult phenotype, be enucleated and have increased expression of β-globin compared to the unmodified cells.

The red blood cells may additionally have a decreased expression of γ-globin compared to the unmodified cells.

The cultured stem cells may be modified by co-transfecting with the transcription factors BCL11A and EKLF or any variants thereof.

The invention further provides a composition comprising red blood cells prepared as described herein and a pharmaceutically acceptable carrier, diluent or excipient.

A blood transfusion pack comprising red blood cells according to the present invention may also be prepared.

The transcription factors may be selected from BCL11A, (BCL11A-XL and other isoforms), EKLF, or modified or tagged versions such as HA-EKLF and any variants thereof that have the desired effect of increasing the expression of β-globin and/or suppress the expression of γ-globin. Other transcription factors involved in globin switching and erythroid maturation could also be used alone or in combination for example, GATA 1, FOG 1, SCL- and any others. In particular, other transcription factors that interact or form a complex with EKLF and BCL11A e.g. GATA 1, FOG1, SOX6.

The red blood cells may be obtained from umbilical cord blood, iPSC or ESC and erythropoietic cells lines derived from any of these stem cell sources and erythropoietic cell lines not derived from these sources but which express fetal globins or progenitor cells from any source. Preferably, the source of the cells is from humans.

According to another aspect of the invention there is provided a method of increasing the expression of β-globin in red blood cells comprising modifying cord blood cells with one or more transcription factors selected from BCL11A and EKLF.

According to a further aspect, there is provided a composition comprising modified red blood cells having an increased expression of β-globin and other erythroid proteins normally expressed in red cells with an adult phenotype compared to the unmodified cells. According to another aspect, there is provided modified red blood cells having an increased expression of β-globin and a decreased expression of γ-globin.

The cells may be modified by inserting appropriate genes into cells using plasmids, viral or other vectors or addition of expression factors, peptides, peptide mimics to make the switch from fetal to adult globin as well as to develop from fetal to adult phenotype and in the case of iPSC and ESC to facilitate the production of enucleated red cells of adult phenotype.

Erythroblasts generated from stem cells from sources such as umbilical cord blood, embryonic stem cells (ESCs) and iPSCs have many advantages over peripheral blood stem cells for the generation of RBCs in vitro for therapeutic purposes, such as greater expansion potential and facilitation of the innovative development of allogeneic and rare blood group products. However these cells express predominantly fetal (γ) rather than adult (β) globin, which have different biochemical and molecular properties. The cells may be sourced from a non-embryonic source.

In order to exploit the proliferative potential of stem cells derived from cord blood, iPSC or ESC for the generation of cultured human red blood cells the inventors have found conditions for inducing the switch from fetal to adult haemoglobin in the cultured erythroid cells. This invention demonstrates that the switch from gamma to beta globin can be effected by co-transfection or co-transduction of erythroid cells derived from cord blood progenitors, iPSC or ESC and erythropoietic cell lines (e.g. K562 cells) expressing fetal globins with two transcription factors (BCL11A and EKLF(KLF1)). EKLF is a key regulator of erythroid maturation affecting many erythroid genes in addition to globin genes (Tallack M R, Perkins A C, IUBMB Life 2010; 62(12):886-890). The invention thereby also provides a general method for converting erythroid progenitors expressing a fetal phenotype to an adult phenotype.

The present inventors had previously transfected an erythropoietic cell line (K562 cells) which expresses fetal globin with the transcription factor EKLF, known to be essential for the switch from γ- to β-globin, induction of the expression of β-globin and for erythropoietic cells development. However, the levels of β-globin induced were minimal. A second transcription factor BCL11A has more recently been shown to be essential for the suppression of the fetal γ-globin in adult erythroblasts, facilitating the switch from γ- to β-globin. The inventors co-transfected K562 cells with both EKLF and BCL11A and found that in combination they induced a robust switch to β-globin expression. The inventors also co-transfected cord blood derived erythroblasts with BCL11A-XL and EKLF and induced a marked increase in β-globin expression.

Of the very small number of transcription factors known to be involved in regulation of the switch from γ to β-globin two critical players identified are BCL11A and EKLF.

BCL11A is a zinc finger (ZF) transcription factor identified from genetic association studies of HbF levels13-16 and shown to be a critical regulator of γ-globin expression in humans[17]. Multiple variants of BCL11A are expressed although the three main forms reported are BCL11A-XL, BCL11A-L and BCL11A-S [17,18]. All variants share a common exon 1, 2 and 3 and part of exon 4, resulting in a variable number of ZFs in each form; exon 4 contributes 6 ZFs to BCL11A-XL, 3 to BCL11A-L and 1 to BCL11A-S all appended to the single ZF encoded by exon 2. In addition, BCL11A-L and -S have additional exon 5, which is absent from BCL11A-XL.

Developmental analysis of human erythroblasts shows full length forms of BCL11A robustly expressed in adult cells, at substantially lower levels in fetal cells and absent in primitive erythroblasts[17], an inverse relationship to the expression of fetal globin (HbF) in these cells. In adult erythroid cells full length BCL11A occupies several discrete regions within the human β-globin cluster including HS3 of the LCR and an intergenic region between Aγ-globin and δ-globin genes[17]. BCL11A also associates with components of the NURD-repressive complex in these cells17. Knock down of BCL11A in human definitive erythroblasts results in increased expression of HbF[17] and reconfiguration of the 3D chromatin loop formation at the β-globin locus such that the γ genes are preferentially associated with the LCR[19]. In addition introduction of a human β-locus transgene into BCL11A knockout mice resulted in impaired silencing of the γ-genes in the definitive erythroid lineage [20]. Together these data support a role for BCL11A as a critical mediator of γ-globin silencing and the developmental switch from HbF to adult (HbA) globin. As such BCL11A represents a potential target for reactivation of HbF in patients with β-hemaglobinopathies. Indeed such an effect has recently been demonstrated in SCD transgenic mice whereby inactivation of BCL11A corrects the hematologic and pathological defects associated with SCD through HbF induction[21].

EKLF (KLF1) is an erythroid specific transcription factor essential for β-globin expression, definitive erythropoiesis and the switch from HbF to HbA22-24. The role of EKLF in β-globin expression has been extensively studied [25]. EKLF null mice die in utero around embryonic day 14-15 due to failure of β-globin gene expression during fetal liver erythropoiesis[22]. β-globin expression is also absent in EKLF null mice containing a human β locus transgene, whereas γ-globin is increased [24]. Similarly, knockdown of EKLF in adult erythroblasts results in an increase in the γ- to β-globin ratio, and notably reduces expression of BCL11A26. Accumulating data show that EKLF also regulates many other erythroid genes and hence plays a critical and central role in erythropoiesis [22, 27-30].

Regulated by post-translational modifications, EKLF modulates both chromatin remodelling and transcriptional activity via interaction with other proteins and complexes [31-34]. EKLF has been shown to interact in vivo with HS2 and HS3 of the LCR as well as with the β-globin proximal promoter [35]. Although the exact mechanism by which EKLF regulates β-globin expression is not yet fully elucidated, data indicate that EKLF plays a central role in promoting interaction of the LCR with the proximal β-globin promoter resulting in β-globin expression in adult erythroid cells[36]. As such targeted knockdown of EKLF has also been proposed as a strategy for activating HbF in individuals with sickle cell disease and β-thalassemia.

As EKLF and BCL11A are critical for the switch to, and expression of adult β-like globin the inventors surprisingly found that erythroid cells intrinsically expressing fetal globins have absent or reduced expression of these transcription factors. Secondly, as knockdown of either EKLF or BCL11A can result in reversal of the globin switch with a concomitant increase in fetal globins, the inventors surprisingly found that conversely induced or increased expression of these transcription factors in cells intrinsically expressing fetal globins induced the switch to adult globin expression.

The globin switch is a major barrier to commercial manufacture of human red cells from umbilical cord, human embryonic stem cells (hESCs), human induced pluripotent stem cells (hiPSCs) and other non-adult haemopoietic stem cells as the generated erythroid cells express fetal rather than adult globin, which has different biochemical properties. In addition, erythroid cells derived from such stem cell sources have a less mature phenotype, differing in the expression of some cell surface antigens to adult RBCs and have defective or poor rates of enucleation. Both EKLF and BCL11A are essential for the developmental switch from fetal (γ- to adult (β) globin and for definitive erythropoiesis, with EKLF regulating many essential erythroid genes including cytoskeleton proteins, membrane proteins and those involved in cell cycle regulation.

Transduction of erythroid cells generated from the above stem cell sources with EKLF and BCL11A was shown to induce the switch from γ- to β-globin and may also induce maturation of the red cells produced to that of the adult red cell phenotype. This has the advantage of resolving the major problem presently incurred with production of red cells from hESCs and hiPSCs where low levels of enucleation are observed in vitro. Overcoming these hurdles will enable the use of such cultured modified red cells of adult phenotype for therapeutic and diagnostic application.

The invention will now be described by way of illustration only in the following examples and accompanying drawings in which:—

FIG. 1 shows expression of BCL11A and EKLF in K562 cells.

(A) Transcripts for the BCL11A variants BCL11A-XL, BCL11A-L and BCL11A-S were compared in K562 cells and erythroblasts differentiated from peripheral blood progenitors by PCR. Two primer sets were used for BCL11A-S and BCL11A-L. (B) Western blot of 20 μg of protein from K562 cells probed with a BCL11A antibody. Total protein from erythroblasts differentiated from peripheral blood progenitors was used as a positive control. (C) EKLF transcripts (left hand panel) and protein (right hand panel) in K562 cells and peripheral blood derived erythroblasts at day 9 in culture as a positive control (Erythroid Ctrl). Membranes were stripped and re-probed with an antibody to tubulin as a protein loading control.

FIG. 2 shows transfection of K562 cells with EKLF and BCL11A induces β-globin expression.

K562 cells were transfected with 5 μg of pCDNA3 Flag-BCL11A-XL (B-XL), 5 μg of pBp HA-EKLF (E) or co-transfected with 5 μg of each plasmid. Cells were collected 20 hours post transfection. (A) Western blot of total protein from transfected and K562 control (Ctrl) cells probed with BCL11A and HA-tag antisera (for EKLF). (B) Transcripts for β-globin in transfected and K562 control cells analysed by qPCR. Relative β-globin expression was normalised to PABPC1 expression and calibrated to K562 control. (C) Western blot of total protein from transfected and K562 control cells probed with a β-globin antibody. All Western blots were stripped and re-probed with an antibody to tubulin as a protein loading control.

FIG. 3 shows transcript levels of β-globin parallels expression of BCL11A and EKLF.

K562 cells were co-transfected with 5 μg of pCDNA3 Flag-BCL11A-XL (B-XL) and 5 μg of pBp HA-EKLF (E). Cells were collected at 24 and 48 hours post transfection. (A) Transcripts for BCL11A, EKLF and β-globin in co-transfected and K562 control (Ctrl) cells at 24 and 48 hours post transfection. Erythroblasts differentiated from peripheral blood progenitors at day 7 in culture were used as a positive control (Erythroid Ctrl). For PCR amplification of EKLF transcripts the forward primer was designed within the HA tag region (B) Western blot of total protein from co-transfected and K562 control cells probed with BCL11A and HA-tag (for EKLF antisera). Blots were stripped and re-probed with an antibody to tubulin as a loading control. (C) Levels of β-globin transcript in co-transfected and K562 control cells at 24 and 48 hours post transfection analysed by qPCR. Relative β-globin expression was normalised to PABPC1 expression and calibrated to K562 control. (D) β- and γ-globin expression profiles as a ratio to total β- and γ-globin in co-transfected and K562 control cells at 24 and 48 hours post transfection.

FIG. 4 shows up-regulation of β-globin transcript with increased levels of BCL11A and EKLF.

K562 cells were transfected with 10 μg of pCDNA3 Flag-BCL11A-XL (B-XL) or 10 μg pBp HA-EKLF (E), or were co-transfected with 5 μg or 10 μg each of both plasmids. Cells were collected at 17 hours post transfection. (A) Western blot of total protein from co-transfected and K562 control (Ctrl) cells probed with BCL11A, HA-tag (for EKLF), (D) β-globin antisera and (E) tubulin. Blots were stripped and re-probed with an antibody to tubulin. (B) Transcripts for β-globin in transfected and K562 control cells analysed by qPCR. Relative β-globin expression was normalised to PABPC1 expression and calibrated to K562 control. (C) β- and γ-globin expression profiles as a ratio to total β- and γ-globin in co-transfected and K562 control cells.

FIG. 5 shows expression of globin isoforms in cord and peripheral blood RBCs and BCL11A and EKLF in erythroblasts cultured from cord blood and peripheral blood progenitors.

(A) Gel showing globin isoforms in mature cord and adult RBCs. (B) Western blot of total protein from cord and peripheral blood derived erythroblasts at day 6, 8 and 11 probed with BCL11A and EKLF antisera. Blots were stripped and re-probed with an antibody to tubulin as a control for protein loading. (C) Graph depicting % cell types observed during ex vivo culture of cord blood (CB) and peripheral blood (PB) derived erythroblasts.

FIG. 6 shows co-transfection of cord blood derived erythroblasts with EKLF and BCL11A increases β-globin expression.

Erythroblasts cultured from cord blood progenitors were co-transfected with 5 μg each of pCDNA3 Flag-BCL11A-XL (B-XL) and pBp HA-EKLF (E). Cells were collected 17 hours post transfection. (A) Western blot of total protein from co-transfected (BX-L: E) and mock (no DNA) transfected control cord blood derived erythroblasts probed with BCL11A and HA-tag (for EKLF) antisera, then stripped and re-probed with β-globin antisera. The blot was stripped again and re-probed with an antibody to tubulin as a protein loading control. (B) Transcripts for β-globin in co-transfected cells analysed by qPCR. Relative β-globin expression was normalised to PABPC1 expression and calibrated to control (no DNA) transfected cord blood cells (n=2). (C) Relative β-globin protein expression in single and co-transfected cells normalised to tubulin expression and calibrated to mock (no DNA) transfected control cells (n=3)

FIG. 7 shows K562 cells 48 hrs after dual transduction of with EKLF and BCL11A-XL.

K562 cells were transduced with the lentiviral constructs pXLG3-mcherry-EKLF and pXLG3-eGFP-BCL11A-XL. Following confocal imaging cells expressing EKLF are shown as red (A), cells expressing BCL11A-XL are shown as green (B) and cells expressing both EKLF and BCL11A are shown as orange/yellow (C).

EXAMPLES

Methods

Example 1—Plasmid Construction

Wild type (WT) EKLF expression plasmid pBabe puro HAII WT EKLF was kindly provided by Dr Belinda Singleton. Briefly, full length EKLF was amplified using the following primers: 5'-GATTACGCTGAATTCTCATGGC-CCACAGCCGAGACC-3' (SEQ ID No:1) and 5'-GA-TACTCGAGAATTCTCAAAGGTGGCGCTTCATG-3' (SEQ ID NO:2), cloned into pCR®2.1-TOPO vector then subsequently sub-cloned into the EcoRI site of pBabe puro HAII (plasmid 14738, Addgene Inc., Cambridge, Mass., US courtesy of the laboratory of Dr Adrienne Cox).

BCL11A expression plasmids pCDNA3-Flag-BCL11A-XL, pCDNA3-Flag-BCL11A-L and pCDNA3-Flag-BCL11A-S were kind gifts from Dr P. Tucker and Dr. Baeck-Seung Lee (Section of Molecular Genetics and Microbiology and Institute of Cellular and Molecular Biology, University of Texas).

Example 2—Cell Culture and Nucleofection

CD34$^+$ cells isolated from umbilical cord blood using the MiniMacs™ magnetic beads separation system (Miltenyi Biotech Ltd, Surrey, UK) were cultured ex vivo for 5-8 days using the three-stage erythroid culture method previously described [37]; IMDM (Source BioScience) containing 3% (v/v) AB Serum (Sigma), 2% (v/v) fetal bovine serum (Hyclone, Fisher Scientific UK Ltd), 10 μg/ml Insulin (Sigma), 3U/ml heparin (Sigma), 200 μg/ml Transferrin (R&D Systems). In the first stage (days 0-8) this was supplemented with 10 ng/ml SCF (Stem cell factor), 1 ng/ml IL-3 and 3U/ml EPO (erythropoietin); in the second stage (days 8-11) with 10 ng/ml SCF, 3U/ml EPO and additional 800 μg/ml iron saturated transferrin and in the final stage (days 11-20) with 3U/ml EPO and additional 800 μg/ml iron saturated transferrin.

K562 cells were obtained from the European Collection of Cell Cultures (Salisbury, UK) and maintained in culture at $2 \times 10^5$ cells/ml in Iscove's modified Dulbecco's Medium with L-Glutamine supplemented with 10% Fetal Calf Serum.

Cord Blood cells and K562 cells were transfected using the Amaxa Nucleofectio® system (Lonza Cologne AG, Cologne, Germany) with Amaxa® Human CD34$^+$ Cell Nucleofector® Kit and Amaxa® Cell Line Nucleofector® Kit V respectively, following the manufacturer's protocols. Briefly, for each nucleofection reaction $1.5-2 \times 10^6$ cells were gently re-suspended in 100 μl Amaxa® Nucleofector® solution with supplement, mixed with 5-10 μg of BCL11A and/or wild type EKLF plasmid DNA and pulsed with a predefined programme (U-008 for Cord Blood cells and T-016 for K562 cells). Transfected cells were transferred into wells of a 12 well plate with 2 ml (final volume) media per sample and maintained at 37° C. in a 5% $CO_2$ humidified incubator.

Example 3—Standard and Quantitative Polymerase Chain Reaction Analysis

A minimum of $5 \times 10^5$ cells were washed twice in 1× Hanks Buffered Saline Solution (HBSS, Sigma-Aldrich) and frozen in RNA Later. Total RNA was extracted and the yield quantified. 400 ng RNA was reverse transcribed into cDNA using SuperScript II reverse transcriptase (Invitrogen, Paisley). BCL11A and EKLF expression were analysed by standard polymerase chain reaction (PCR) whilst β-globin and γ-globin gene expression were analysed by quantitative (q)PCR. All methods have been previously described [38]. Sequences used in PCR and qPCR are as follows:

```
BCL11A-XL:
                                        (SEQ ID NO: 3)
5'-AGATCCCTTCCTTAGCTTCG-3'
and
```

-continued

```
                                    (SEQ ID NO: 4)
5'-TCAACACTCGATCACTGTGC-3';

BCL11A-L:
                                    (SEQ ID NO: 5)
5'-GACGATGGCACTGTTAATGG-3'
and
                                    (SEQ ID NO: 6)
(1) 5'-GGGTGTGTGAAGAACAAGTG-3', (SEQ ID NO: 7)
(2) 5'-AATGGGGGTGTGTGAAGAAC-3';

BCL11A-S:
                                    (SEQ ID NO: 8)
5'- CATGACCTCCTCACCTGTGG-3'
and (SEQ ID NO: 9)
(1) 5'-GGTGTGTGAAGAACCCGCGG-3', (SEQ ID NO: 10)
(2) 5'-ATGGGGGTGTGTGAAGAACC-3';

EKLF:
                                    (SEQ ID NO: 11)
5'-GCCCTCCATCAGCACACT-3'
and (SEQ ID NO: 12)
5'-GATCCTCCGAACCCAAAAG-3';

HA-EKLF:
                                    (SEQ ID NO: 13)
5'-ATATGATGTGCCCGACTATGC-3'
(primer sequence within HA tag)
and (SEQ ID NO: 14)
5'-GATCCTCCGAACCCAAAAG-3';

HBB (PCR): HBB (PCR):
                                    (SEQ ID NO: 15)
5'-CTTTAGTGATGGCCTGGCTC-3'
and (SEQ ID NO: 16)
5'-GGCAGAATCCAGATGCTCAA-3';

HBB (qPCR):
                                    (SEQ ID NO: 17)
5'-GCAAGGTGAACGTGGATGAAG-3'
and (SEQ ID NO: 18)
5'-TCACCTTAGGGTTGCCCATAACT-3';

HBG:
                                    (SEQ ID NO: 19)
5'-GGGCAAGGTGAATGTGGAAGAT-3'
and (SEQ ID NO: 20)
5'-GGGTCCATGGGTAGACAACCA-3';

PABPC1:
                                    (SEQ ID NO: 21)
5'-AGCTGTTCCCAACCCTGTAATC-3'
and (SEQ ID NO: 22)
5'-GGATAGTATGCAGCACGCTTCTG-3'.
```

For qPCR analysis, all target gene sequences have been normalised to PABPC1 and calibrated to a control denoted in the figure legend.

Example 4—Western Blot Analysis

Transfected K562 cells and Cord Blood cells were prepared for Western Blot analysis by washing cell pellets twice in 1×HBSS then lysing whole cells in solubilisation buffer (20 mM Tris HCl pH 7.5, 150 mM NaCl, 10% Glycerol, 1% Triton, 0.1% SDS, 1× Complete protease inhibitor, and 2 mM PMSF) for 1 hour followed by 1 hour treatment with 12.5 U Benzonase® nuclease (Novagen, Damstadt, Germany). Protein (3-15 µg) quantified by BioRad Protein Assay Dye reagent was resolved by 8%, 12% or 18% Sodium Dodecyl Sulphate (SDS)-Polyacrylamide Gel Electrophoresis (PAGE) and transferred to PVDF membrane. EKLF, BCL11A and β-globin were detected by incubating with the following antibodies; HA.II (16B12 Covance, Crawley, UK) or EKLF (H-210, Santa Cruz Biotechnology, Santa Cruz, Calif.), Ctip1 (14B5, Abcam, Cambridge, UK) and Hemoglobin β (37-8 Santa Cruz Biotechnology, Santa Cruz, Calif.) for a minimum of 1 hour. Protein bands were quantified using BIORAD Quantity One software version 4.5.1.

Example 5—Lentivirus Preparation and Cell Transduction

The EKLF and BCL11A-XL coding regions were amplified by PCR and inserted into pXLG3-eGFP or pXLG3-mcherry lentiviral vector using In-Fusion cloning system (Clontech). HEK 293T cells were transfected with constructs pMDG2 (viral coat), pCMVR8.91 (packaging protein) and pXLG3-eGFP-BCL11A-XL and pXLG3-mcherry-EKLF using Polyethylenimine (PEI). PEI/DNA solutions were incubated with the cells for 4 hours, after which the media was replaced. After 48 hours media containing the virus was filtered and aliquoted. Erythroid cells were incubated with 1 ml of virus with the addition of polybrene at 8 µg/ml. Cells were harvested at 48 hours and fixed with 4% paraformaldehyde onto poly-L-lysine coated cover slips and imaged using confocal microscopy.

Results

Example 6—Expression of BCL11A in K562 Cells

Expression of BCL11A-XL, BCL11A-L and BCL11A-S transcripts was determined in K562 cells, an erythropoietic cell line that expresses HbE and HbF but not HbA, and erythroblasts cultured from peripheral blood CD34+ cells at day 9 in culture as a positive control, by PCR using primers specific for each BCL11A variant. Transcripts for all 3 BCL11A variants were detected in the erythroblasts but no transcripts were detected in K562 cells (FIG. 1A). In addition full length BCL11A protein was readily detected in the erythroid but neither full length nor shorter variants of BCL11A protein were detected in the K562 cells (FIG. 1B). Transcripts for KLF-1 were detected in K562 cells, but at a low level compared to the day 9 erythroblasts, however no KLF-1 protein was detected (FIG. 1C). Hence K562 cells are considered null for EKLF. Lack of β-globin expression in K562 cells therefore correlates with the lack of BCL11A and EKLF.

Example 7—Transfection of K562 Cells with EKLF and BCL11A-XL Induces β-Globin Expression K562 cells were transiently transfected with pCDNA3-Flag-BCL11A-XL (BCL11A-XL; 5 µg), pBp HA-EKLF (HA-EKLF; 5 ug) or co-transfected with both plasmids (5 µg of each). Cells were collected 20 hrs post transfection and analysed for BCL11A, EKLF and β-globin expression. Cells transfected with BCL11A-XL or HA-EKLF expressed the respective proteins, co-transfected cells expressed both proteins (FIG. 2A). Levels of β-globin transcript in the single and co-transfected cells were then analysed by qPCR. Negligible transcripts for β-globin were detected in BCL11A transfected cells whilst a small increase (3 fold that in untransfected K562 cells) was detected in the HA-EKLF transfectants (FIG. 2B). However, on co-transfection with BCL11A-XL and HA-EKLF, transcript levels for β-globin increased 168 fold compared to untransfected cells (FIG. 2B) with a notable increase in the levels of β-globin protein (7.9 fold when normalized to tubulin and compared with untransfected K562 cells; FIG. 2C).

Example 8—Expression of β-Globin Parallels Expression Levels of BCL11A and EKLF

Figure 3A:
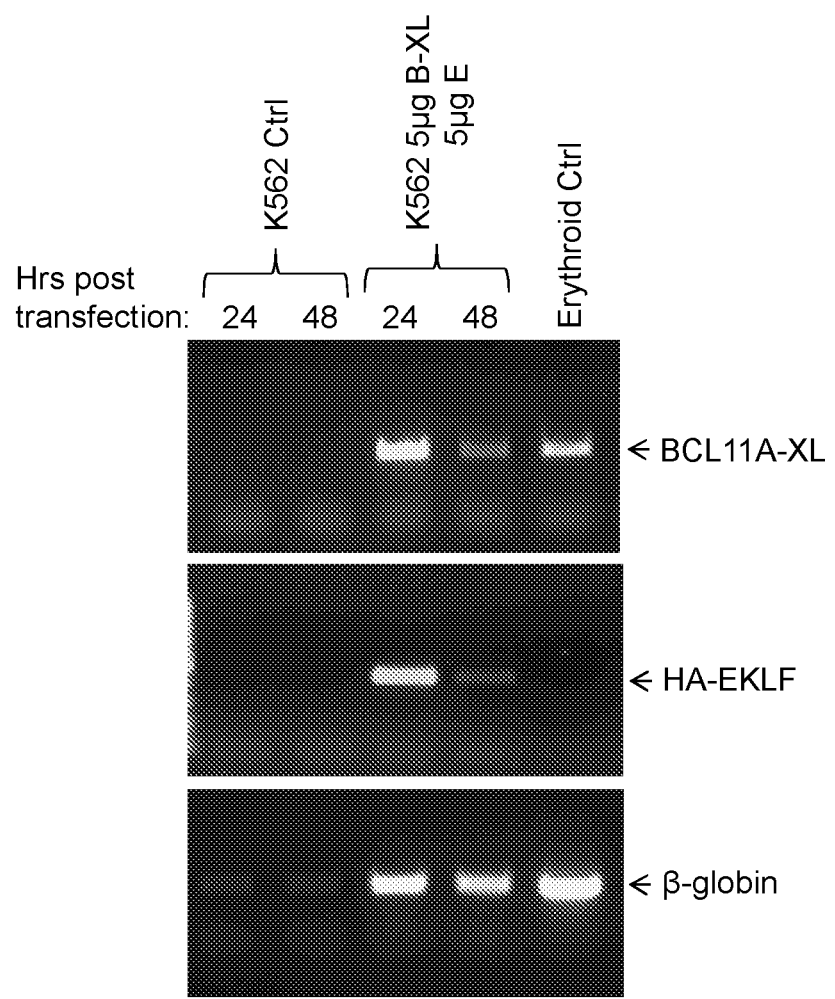

To determine if expression levels of β-globin increased with time post transfection K562 cells co-transfected with BCL11A-XL and HA-EKLF (5 μg of each) were analysed for BCL11A, EKLF and β-globin at 24 and 48 hrs post transfection. Following transfection transcripts and protein for BCL11A and EKLF were readily detected but their levels decreased between 24 and 48 hrs post transfection (FIGS. 3A and B). Expression of β-globin was again markedly higher in co-transfected compared to untransfected cells but transcript levels also decreased from 24 to 48 hrs post transfection, paralleling the decrease in levels of BCL11A and EKLF (FIGS. 3A and C). In addition, the ratio of γ- to β-globin expression decreased following transfection but increased slightly between 24 and 48 hrs post transfection (FIG. 3D).

Hence co-transfection of just BCL11A-XL and EKLF is clearly sufficient to induce and regulate expression of β-globin in these cells.

Figure 4A:
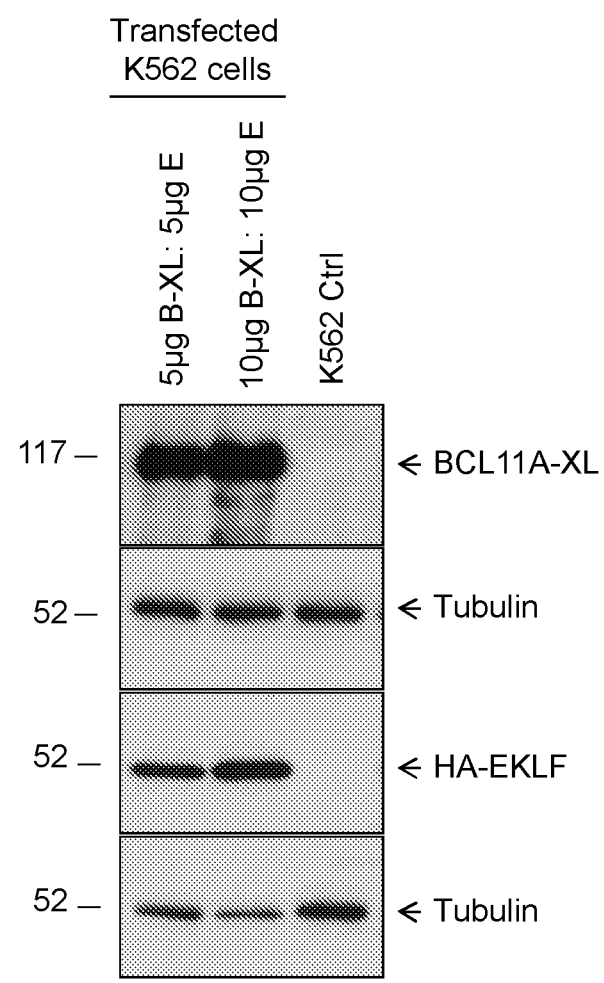

Example 9—Transfection of K562 Cells with Increased Amount of BCL11A-XL and EKLF Further Enhances Expression of β-Globin In an attempt to increase the level of expression of β-globin in co-transfected K562 cells we increased the amount of DNA used for transfection from 5 μg to 10 μg of each plasmid. We also compared transcript levels at different times post transfection and found 17 hrs to be optimal in this example (data not shown). Co-transfection with the higher concentration of DNA increased the level of BCL11A and EKLF in cells (FIG. 4A). K562 cells were initially transfected with BCL11A-XL (10 μg) or HA-EKLF (10 μg) and analysed for β-globin expression 17 hrs post transfection by qPCR. Transfection with just BCL11A-XL or HA-EKLF increased the level of β-globin transcript by 5.9 and 7.5 fold respectively compared to untransfected K562 cells (FIG. 4B). Co-transfection with 5 ug each of BCL11A-XL and HA-EKLF increased the levels of β-globin transcript by 305+/−156.9 fold (n=2) (FIG. 4B). However co-transfection with 10 μg each of BCL11A-XL and HA-EKLF increased the levels of β-globin transcript by 887+/−143 fold (n=2) compared to untransfected K562 cells (FIG. 4B). Beta globin protein was detected in K562 cells following transfection with both concentrations of DNA (FIG. 4A). The ratio of γ- to β-globin expression again decreased on co-transfection with BCL11A-XL and EKLF, but only a very small decrease in the ratio was detected on transfection with 10 μg compared to 5 μg of each plasmid (FIG. 4C).

Co-transfection of cells with pCDNA3-Flag-BCL11A-L or pCDNA3-Flag-BCL11A-S along with HA-EKLF (10 μg of each) did not increase expression levels of β-globin compared to cells transfected with EKLF alone (data not shown).

Hence BCL11A-XL and EKLF individually have a modest effect on induction of β-globin expression. However co-transfection of K562 cells with BCL11A-XL and EKLF has a robust effect on the induction of β-globin expression in these cells.

Example 10—Expression of BCL11A and EKLF in Erythroblasts Differentiated from Cord Blood Compared to Peripheral Blood Progenitors Erythroblasts differentiated from cord blood CD34$^+$ progenitors express predominantly HbF (~65%) in contrast to erythroblasts differentiated from peripheral blood CD34$^+$ cells which express predominately HbA (~94%), similar to normal adult erythroid cells. FIG. 5A shows the globin isoforms present in adult RBCs compared to cord RBCs.

Switching the globin expression profile in cord blood erythroblasts to that of adult erythroid cells is a highly desirable objective as these cells have excellent expansion capacity and hence are attractive progenitors for in vitro systems aimed at generating RBCs for transfusion purposes.

Figure 5C:
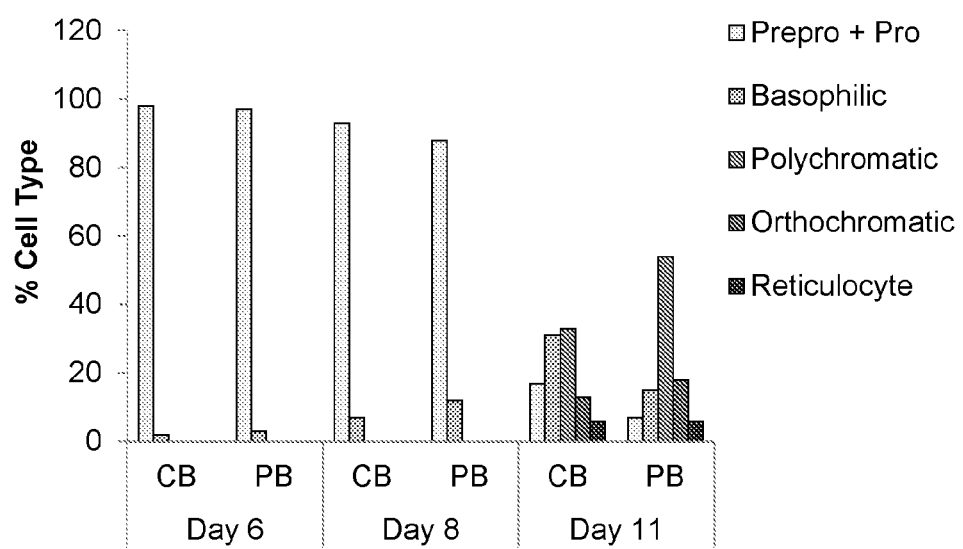

The levels of BCL11A and EKLF were shown to be lower in erythroblasts derived from cord blood compared to peripheral blood CD34$^+$ cells consistent with their globin expression profiles. The level of BCL11A and EKLF in erythroblasts cultured from cord and peripheral blood progenitors were compared at various time points in culture by western blot with specific BCL11A and EKLF antisera. Levels of EKLF (normalized to tubulin control) in cord blood erythroblasts were significantly lower at all-time points examined than in peripheral blood erythroblasts; 41, 10 and 2.5 fold for days 6, 8 and 11 respectively (FIG. 5B). The difference in level declined as synchronicity between the two cultures decreased with reduction in the number of proliferative prepro- and pro-normoblasts and increase in differentiating erythroblasts in the peripheral blood compared to the cord blood derived cells notable by day 11 (FIG. 5C). Levels of BCL11A in erythroblasts at day 6 and 8 in culture were 9 and 6 fold lower respectively in cord compared to peripheral blood derived erythroblasts (FIG. 5B). At day 11 in culture the levels of BCL11A had declined and were extremely low in both cell populations. Hence the levels of both BCL11A and EKLF are consistently lower in cord blood derived compared to peripheral blood derived erythroblasts which correlates with the expression ratio of γ- to β-globin in these cells.

Example 11—Co-Transfection of Cord Blood Derived Erythroblasts with BCL11A-XL and EKLF Increases the Expression of β-Globin Increasing the expression of BCL11A and EKLF in cord blood erythroblasts was found to increase the expression of adult β-globin.

Figure 6A:
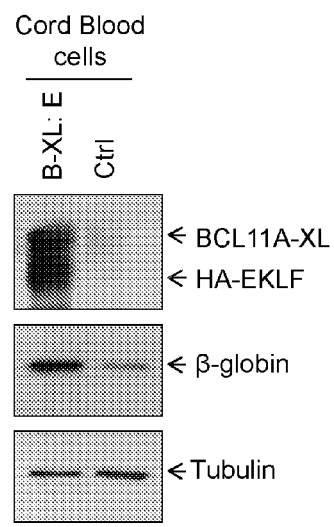

Erythroblasts cultured from cord blood progenitors were co-transfected with BCL11A-XL and HA-EKLF. The transfection programme resulted in a significant amount of cell death (~50%). However, following transfection the levels of BCL11A and HA-EKLF protein were markedly increased as compared to that in cells subjected to nucleofection in the absence of DNA (FIG. 6A). Correspondingly, the levels of β-globin transcript increased by 4.9±1.3 (FIG. 6B; n=2). We also analysed the levels of β-globin protein in cells transfected with just BCL11A-XL or HA-KLF-1, as well as in co-transfected cells. The level of β-globin (normalized to tubulin control) in cells transfected with BCL11A or KLF-1 showed no clear increase (1.1±0.14 and 1.23±0.18 fold respectively compared to control cells). However cells co-transfected with BCL11A and KLF-1 showed a 5.1±2 fold (n=3) increase in the level of β-globin protein, compared to control cells (FIGS. 6A and C).

These data clearly demonstrate that increasing the expression of BCL11A and EKLF in cord blood derived erythroblasts results in a significant increase in the expression of β-globin. The increase in β-globin expression obtained was significant, as a 5 fold decline in β-globin mRNA has been reported on KLF1 knock out [22].

Example 12—Delivery of Genes for EKLF and BCL11A into Erythroid Cells Using Viral Transduction Procedures A more efficient system for delivery of the genes for both EKLF and BCL11A into erythroid cells was developed. Lentivirus constructs for both BCL11A and EKLF genes using the lentivirus pSEW-GFP plasmid were made (backbone plasmid, viral packaging plasmid, transfer vector plasmid and 293T cells were donated by the School of Biochemistry). To verify viability of the approach erythropoietic cell line, K562 cells were transduced simultaneously with the lentiviral constructs pXLG3-mcherry-EKLF (FIG. 7A) and pXLG3-eGFP-BCL11A-XL (FIG. 7B). Transduction efficiency was routinely >80%. Overlay of the EKLF and BCL11A confocal images showed >40% dual expression of the transcription factors (FIG. 7C).

Cord blood erythroblasts were co-transduced at day 5 post isolation with the EKLF and BCL11A constructs. Cells were isolated at day 8 to 9 for analysis of globin expression by qPCR and western blot.

Erythroblasts generated from cord blood CD34+ cells being of fetal origin are inherently less mature than erythroblasts generated from adult CD34+ cells, differing in the expression of some cell surface RBC antigens; for example the i rather than adult I antigen.

Following the dual transduction protocol, cells were allowed to differentiate down the erythroid pathway and were analysed for morphological characteristics and enucleation, screened for a range of cell surface red cell antigens by flow cytometry using a panel of specific antisera and for functional properties including oxygen binding and release which are key measures of an adult phenotype. Induced expression of EKLF and BCL11A induced maturation of cord blood cells to an adult phenotype and facilitated enucleation.

REFERENCES

[1] Bender, M. A.; Bulger, M.; Close, J.; Groudine, M. Beta-globin gene switching and DNase I sensitivity of the endogenous beta-globin locus in mice do not require the locus control region. Mol Cell 5:387-393; 2000.

[2] Forrester, W. C.; Thompson, C.; Elder, J. T.; Groudine, M. A developmentally stable chromatin structure in the human beta-globin gene cluster. Proceedings of the National Academy of Sciences of the United States of America 83:1359-1363; 1986.

[3] Grosveld, F.; van Assendelft, G. B.; Greaves, D. R.; Kollias, G. Position-independent, high-level expression of the human beta-globin gene in transgenic mice. Cell 51:975-985; 1987.

[4] Tuan, D.; Solomon, W.; Li, Q.; London, I. M. The "beta-like-globin" gene domain in human erythroid cells. Proceedings of the National Academy of Sciences of the United States of America 82:6384-6388; 1985.

[5] Noordermeer, D.; de Laat, W. Joining the loops: beta-globin gene regulation. IUBMB life 60:824-833; 2008.

[6] Wijgerde, M.; Grosveld, F.; Fraser, P. Transcription complex stability and chromatin dynamics in vivo. Nature 377:209-213; 1995.

[7] Dillon, N.; Grosveld, F. Human gamma-globin genes silenced independently of other genes in the beta-globin locus. Nature 350:252-254; 1991.

[8] Raich, N.; Enver, T.; Nakamoto, B.; Josephson, B.; Papayannopoulou, T.; Stamatoyannopoulos, G. Autonomous developmental control of human embryonic globin gene switching in transgenic mice. Science 250:1147-1149; 1990.

[9] Sabatino, D. E.; Cline, A. P.; Gallagher, P. G.; Garrett, L. J.; Stamatoyannopoulos, G.; Forget, B. G.; Bodine, D. M. Substitution of the human beta-spectrin promoter for the human agamma-globin promoter prevents silencing of a linked human beta-globin gene in transgenic mice. Molecular and cellular biology 18:6634-6640; 1998.

[10] Tanavde, V. M.; Malehorn, M. T.; Lumkul, R.; Gao, Z.; Wingard, J.; Garrett, E. S.; Civin, C. I. Human stem-progenitor cells from neonatal cord blood have greater hematopoietic expansion capacity than those from mobilized adult blood. Exp Hematol 30:816-823; 2002.

[11] Kaufman, D. S. Toward clinical therapies using hematopoietic cells derived from human pluripotent stem cells. Blood 114:3513-3523; 2009.

[12] Peyrard, T.; Bardiaux, L.; Krause, C.; Kobari, L.; Lapillonne, H.; Andreu, G.; Douay, L. Banking of pluripotent adult stem cells as an unlimited source for red blood cell production: potential applications for alloimmunized patients and rare blood challenges. Transfus Med Rev 25:206-216; 2011.

[13] Lettre, G.; Sankaran, V. G.; Bezerra, M. A.; Araujo, A. S.; Uda, M.; Sanna, S.; Cao, A.; Schlessinger, D.; Costa, F. F.; Hirschhorn, J. N.; Orkin, S. H. DNA polymorphisms at the BCL11A, HBS1L-MYB, and beta-globin loci associate with fetal haemoglobin levels and pain crises in sickle cell disease. Proceedings of the National Academy of Sciences of the United States of America 105:11869-11874; 2008.

[14] Menzel, S.; Garner, C.; Gut, I.; Matsuda, F.; Yamaguchi, M.; Heath, S.; Foglio, M.; Zelenika, D.; Boland, A.; Rooks, H.; Best, S.; Spector, T. D.; Farrall, M.; Lathrop, M.; Thein, S. L. A QTL influencing F cell production maps to a gene encoding a zinc-finger protein on chromosome 2p15. Nature genetics 39:1197-1199; 2007.

[15] Sedgewick, A. E.; Timofeev, N.; Sebastiani, P.; So, J. C.; Ma, E. S.; Chan, L. C.; Fucharoen, G.; Fucharoen, S.; Barbosa, C. G.; Vardarajan, B. N.; Farrer, L. A.; Baldwin, C. T.; Steinberg, M. H.; Chui, D. H. BCL11A is a major HbF quantitative trait locus in three different populations with beta-hemoglobinopathies. Blood Cells Mol Dis 41:255-258; 2008.

[16] Uda, M.; Galanello, R.; Sanna, S.; Lettre, G.; Sankaran, V. G.; Chen, W.; Usala, G.; Busonero, F.; Maschio, A.; Albai, G.; Piras, M. G.; Sestu, N.; Lai, S.; Dei, M.; Mulas, A.; Crisponi, L.; Naitza, S.; Asunis, I.; Deiana, M.; Nagaraja, R.; Perseu, L.; Satta, S.; Cipollina, M. D.; Sollaino, C.; Moi, P.; Hirschhorn, J. N.; Orkin, S. H.; Abecasis, G. R.; Schlessinger, D.; Cao, A. Genome-wide association study shows BCL11A associated with persistent fetal haemoglobin and amelioration of the phenotype of beta-thalassemia. Proceedings of the National Academy of Sciences of the United States of America 105: 1620-1625; 2008.

[17] Sankaran, V. G.; Menne, T. F.; Xu, J.; Akie, T. E.; Lettre, G.; Van Handel, B.; Mikkola, H. K.; Hirschhorn, J. N.; Cantor, A. B.; Orkin, S. H. Human fetal haemoglobin expression is regulated by the developmental stage-specific repressor BCL11A. Science 322:1839-1842; 2008.

[18] Liu, H.; Ippolito, G. C.; Wall, J. K.; Niu, T.; Probst, L.; Lee, B. S.; Pulford, K.; Banham, A. H.; Stockwin, L.; Shaffer, A. L.; Staudt, L. M.; Das, C.; Dyer, M. J.; Tucker, P. W. Functional studies of BCL11A: characterization of the conserved BCL11A-XL splice variant and its interaction with BCL6 in nuclear paraspeckles of germinal center B cells. Mol Cancer 5:18; 2006.

[19] Xu, J.; Sankaran, V. G.; Ni, M.; Menne, T. F.; Puram, R. V.; Kim, W.; Orkin, S. H. Transcriptional silencing of {gamma}-globin by BCL11A involves long-range interactions and cooperation with SOX6. Genes & development 24:783-798; 2010.

[20] Sankaran, V. G.; Xu, J.; Ragoczy, T.; Ippolito, G. C.; Walkley, C. R.; Maika, S. D.; Fujiwara, Y.; Ito, M.; Groudine, M.; Bender, M. A.; Tucker, P. W.; Orkin, S. H. Developmental and species-divergent globin switching are driven by BCL11A. Nature 460:1093-1097; 2009.

[21] Xu, J.; Peng, C.; Sankaran, V. G.; Shao, Z.; Esrick, E. B.; Chong, B. G.; Ippolito, G. C.; Fujiwara, Y.; Ebert, B. L.; Tucker, P. W.; Orkin, S. H. Correction of Sickle Cell Disease in Adult Mice by Interference with Fetal Hemoglobin Silencing. Science 334:993-996; 2011.

[22] Hodge, D.; Coghill, E.; Keys, J.; Maguire, T.; Hartmann, B.; McDowall, A.; Weiss, M.; Grimmond, S.; Perkins, A. A global role for EKLF in definitive and primitive erythropoiesis. Blood 107:3359-3370; 2006.

[23] Miller, I. J.; Bieker, J. J. A novel, erythroid cell-specific murine transcription factor that binds to the CACCC element and is related to the Kruppel family of nuclear proteins. Molecular and cellular biology 13:2776-2786; 1993.

[24] Wijgerde, M.; Gribnau, J.; Trimborn, T.; Nuez, B.; Philipsen, S.; Grosveld, F.; Fraser, P. The role of EKLF in human beta-globin gene competition. Genes & development 10:2894-2902; 1996.

[25] Bieker, J. J. Probing the onset and regulation of erythroid cell-specific gene expression. The Mount Sinai journal of medicine, New York 72:333-338; 2005.

[26] Zhou, D.; Liu, K.; Sun, C. W.; Pawlik, K. M.; Townes, T. M. KLF1 regulates BCL11A expression and gamma- to beta-globin gene switching. Nature genetics 42:742-744; 2010.

[27] Drissen, R.; von Lindern, M.; Kolbus, A.; Driegen, S.; Steinlein, P.; Beug, H.; Grosveld, F.; Philipsen, S. The erythroid phenotype of EKLF-null mice: defects in haemoglobin metabolism and membrane stability. Molecular and cellular biology 25:5205-5214; 2005.

[28] Funnell, A. P.; Maloney, C. A.; Thompson, L. J.; Keys, J.; Tallack, M.; Perkins, A. C.; Crossley, M. Erythroid Kruppel-like factor directly activates the basic Kruppel-like factor gene in erythroid cells. Molecular and cellular biology 27:2777-2790; 2007.

[29] Pilon, A. M.; Arcasoy, M. O.; Dressman, H. K.; Vayda, S. E.; Maksimova, Y. D.; Sangerman, J. I.; Gallagher, P. G.; Bodine, D. M. Failure of terminal erythroid differentiation in EKLF-deficient mice is associated with cell cycle perturbation and reduced expression of E2F2. Molecular and cellular biology 28:7394-7401; 2008.

[30] Singleton, B. K.; Burton, N. M.; Green, C.; Brady, R. L.; Anstee, D. J. Mutations in EKLF/KLF1 form the molecular basis of the rare blood group In(Lu) phenotype. Blood 112:2081-2088; 2008.

[31] Armstrong, J. A.; Bieker, J. J.; Emerson, B. M. A SWI/SNF-related chromatin remodeling complex, E-RC1, is required for tissue-specific transcriptional regulation by EKLF in vitro. Cell 95:93-104; 1998.

[32] Ouyang, L.; Chen, X.; Bieker, J. J. Regulation of erythroid Kruppel-like factor (EKLF) transcriptional activity by phosphorylation of a protein kinase casein kinase II site within its interaction domain. The Journal of biological chemistry 273:23019-23025; 1998.

[33] Zhang, W.; Bieker, J. J. Acetylation and modulation of erythroid Kruppel-like factor (EKLF) activity by interaction with histone acetyltransferases. Proceedings of the National Academy of Sciences of the United States of America 95:9855-9860; 1998.

[34] Zhang, W.; Kadam, S.; Emerson, B. M.; Bieker, J. J. Site-specific acetylation by p300 or CREB binding protein regulates erythroid Kruppel-like factor transcriptional activity via its interaction with the SWI-SNF complex. Molecular and cellular biology 21:2413-2422; 2001.

[35] Im, H.; Grass, J. A.; Johnson, K. D.; Kim, S. I.; Boyer, M. E.; Imbalzano, A. N.; Bieker, J. J.; Bresnick, E. H. Chromatin domain activation via GATA-1 utilization of a small subset of dispersed GATA motifs within a broad chromosomal region. Proceedings of the National Academy of Sciences of the United States of America 102: 17065-17070; 2005.

[36] Drissen, R.; Palstra, R. J.; Gillemans, N.; Splinter, E.; Grosveld, F.; Philipsen, S.; de Laat, W. The active spatial organization of the beta-globin locus requires the transcription factor EKLF. Genes & development 18:2485-2490; 2004.

[37] Griffiths R E et al. Maturing human reticulocytes reduce plasma membrane by endocytosis of Glycophorin A-containing vacuoles which fuse with autophagosomes and exocytose. Blood 2012 Jun. 28; 119(26):6296-306

The invention claimed is:

1. A method of producing adult red blood cells, the method comprising:
   culturing, in a defined medium, human stem cells that express fetal haemoglobin or cells obtained from a human erythropoietic cell line that express fetal haemoglobin,
   transfecting the cultured cells with at least one expression vector comprising a nucleotide sequence encoding transcription factor BCL11A operably linked to an expression control sequence and a nucleotide sequence encoding transcription factor EKLF operably linked to an expression control sequence, wherein expression of the BCL11A and the EKLF increases expression of adult β-globin in the transfected cells, thereby converting the transfected cells into the adult red blood cells.

2. The method according to claim 1,
   wherein the method includes a further step of enucleation of the adult red blood cells, and
   where the human stem cells or the cells obtained from a human erythropoeitic cell line are obtained from induced pluripotent stem cells.

3. The method according to claim 1, wherein the human stem cells are obtained as CD34+ cells.

4. The method according to claim 1, wherein the BCL11A is an isoform of BCL11A[M] or the EKLF is a tagged form of EKLF.

5. The method according to claim 1, wherein the human stem cells or the cells obtained from a human erythropoietic cell line are obtained from umbilical cord blood, induced pluripotent stem cells, erythropoietic stem cells, or an erythropoietic cell line.

6. The method according to claim 1, wherein the defined culture medium comprises at least one of serum, fetal bovine serum, insulin, heparin, and transferrin.

7. The method according to claim 6, wherein the medium is supplemented with at least one of stem cell factor (SCF), erythropoietin (EPO), and iron saturated transferrin.

8. The method according to claim 1, wherein the transcription factor BCL11A is isoform BCL11A-XL.

9. The method according to claim 1, wherein the at least one expression vector is a lentiviral vector.

10. The method according to claim 1, wherein the human stem cells or the cells obtained from a human erythropoeitic cell line are human induced pluripotent stem cells (iPSCs).

11. The method according to claim 1, the wherein the cultured cells are additionally transfected with one or more transcription factors selected from GATA 1, FOG 1, SCL, and SOX6.

12. Isolated red blood cells prepared according to the method according to claim 1, wherein the isolated red blood cells comprise the at least one expression vector.

13. A composition comprising the isolated red blood cells according to claim 12 and a pharmaceutically acceptable carrier, diluent or excipient.

14. A blood transfusion pack comprising the isolated red blood cells according to claim 12.

15. Isolated red blood cells, prepared from human stem cells or cells from a human erythropoietic cell line comprising an expression vector which comprises a nucleotide sequence encoding transcription factor BCL11A operably linked to an expression control sequence and an expression vector which comprises a nucleic acid comprising a nucleotide sequence encoding transcription factor EKLF operably linked to an expression control sequence, wherein the isolated red blood cells have increased expression of β-globin compared to the human stem cells or the cells from a human erythropoietic cell line.

16. The isolated red blood cells according to claim 15, wherein the BCL11A isoform is BCL11A-XL.

17. A composition comprising the isolated red blood cells according to claim 16 and a pharmaceutically acceptable carrier, diluent or excipient.

18. A method of producing adult red blood cells, the method comprising:
   culturing, in a defined medium, human stem cells that express γ-globin and fetal haemoglobin or cells obtained from a human erythropoietic cell line-that express γ-globin and fetal haemoglobin,
   converting the cultured cells into adult red blood cells by transfecting the cultured cells with at least one expression vector comprising a nucleotide sequence encoding transcription factor BCL11A operably linked to an expression control sequence and a nucleotide sequence encoding transcription factor EKLF operably linked to an expression control sequence, wherein expression of the BCL11A and the EKLF increases expression of adult β-globin in the transfected cells, and decreases the expression of the γ-globin and the fetal haemoglobin, thereby converting the transfected cells into the adult red blood cells.

\* \* \* \* \*